(12) United States Patent
Ignjatovic et al.

(10) Patent No.: US 11,899,141 B2
(45) Date of Patent: *Feb. 13, 2024

(54) ULTRASOUND SYSTEM FOR HIGH-SPEED AND HIGH RESOLUTION IMAGING APPLICATIONS

(71) Applicant: University of Rochester, Rochester, NY (US)

(72) Inventors: Zeljko Ignjatovic, Rochester, NY (US); Michael Huang, Rochester, NY (US); Swetha George, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/305,421

(22) Filed: Jul. 7, 2021

(65) Prior Publication Data
US 2021/0333379 A1 Oct. 28, 2021

Related U.S. Application Data

(62) Division of application No. 15/529,174, filed as application No. PCT/US2015/065722 on Dec. 15, 2015, now Pat. No. 11,092,680.
(Continued)

(51) Int. Cl.
*A61B 8/08* (2006.01)
*A61B 8/00* (2006.01)
(Continued)

(52) U.S. Cl.
CPC ............ *G01S 7/52047* (2013.01); *A61B 8/14* (2013.01); *A61B 8/4472* (2013.01);
(Continued)

(58) Field of Classification Search
CPC ............ G01S 7/52047; G01S 15/8915; G01S 15/8918; G01S 15/8959; G01S 7/003;
(Continued)

(56) References Cited

U.S. PATENT DOCUMENTS

| 8,818,064 B2 | 8/2014 | Walker et al. |
| 2007/0083114 A1 | 4/2007 | Yang et al. |

(Continued)

FOREIGN PATENT DOCUMENTS

WO 2011/163475 12/2011

OTHER PUBLICATIONS

PCT/US15/65722, Dec. 15, 2015, Expired.
(Continued)

*Primary Examiner* — Yi-Shan Yang
*Assistant Examiner* — Alexei Bykhovski
(74) *Attorney, Agent, or Firm* — Ping Wang; Rimon Law

(57) ABSTRACT

An ultrasound imaging system includes an array of ultrasound transducer elements chat send ultrasound energy into an object when energized for respective transmission time periods and provide responses to ultrasound energy emitted from the object for respective reception time periods, a reception modulation circuit modulating the responses with irregular sequences of modulation coefficients, a combiner circuit combining the modulated responses, and an image reconstruction processor configured to computer-process the combined modulated responses into one or more images of the object.

7 Claims, 9 Drawing Sheets

Related U.S. Application Data

(60) Provisional application No. 62/094,654, filed on Dec. 19, 2014.

(51) Int. Cl.
*A61B 8/14* (2006.01)
*G01S 7/52* (2006.01)
*G01S 15/89* (2006.01)
*G01S 7/00* (2006.01)

(52) U.S. Cl.
CPC .......... *A61B 8/4483* (2013.01); *A61B 8/5207* (2013.01); *A61B 8/565* (2013.01); *G01S 15/8915* (2013.01); *G01S 15/8918* (2013.01); *G01S 15/8959* (2013.01); *G01S 7/003* (2013.01); *G01S 7/52096* (2013.01); *G01S 15/8925* (2013.01); *G01S 15/8993* (2013.01)

(58) Field of Classification Search
CPC ............. G01S 7/52096; G01S 15/8925; G01S 15/8993; A61B 8/14; A61B 8/4472; A61B 8/4483; A61B 8/5207; A61B 8/565
See application file for complete search history.

(56) References Cited

U.S. PATENT DOCUMENTS

| | | | |
|---|---|---|---|
| 2007/0167781 A1 | 7/2007 | Vortman et al. | |
| 2007/0208254 A1 | 9/2007 | Johnson et al. | |
| 2012/0016921 A1* | 1/2012 | Davenport | H03M 7/30 708/322 |
| 2012/0083695 A1 | 4/2012 | Napolitano et al. | |
| 2013/0096433 A1 | 4/2013 | Lemmerhirt et al. | |
| 2013/0123635 A1 | 5/2013 | Wegner | |
| 2014/0056104 A1 | 2/2014 | Buechler et al. | |
| 2014/0180112 A1 | 6/2014 | Rothberg et al. | |
| 2014/0180176 A1* | 6/2014 | Rothberg | A61B 8/4488 601/3 |
| 2014/0269206 A1* | 9/2014 | Mo | A61B 8/488 367/138 |
| 2015/0265250 A1* | 9/2015 | Madore | G01S 15/8977 600/440 |
| 2015/0351720 A1* | 12/2015 | Ikeda | A61B 8/5207 600/447 |
| 2017/0363725 A1 | 12/2017 | Ignjatociv et al. | |

OTHER PUBLICATIONS

U.S. Appl. No. 15/529,174, filed May 24, 2017, Pending.
U.S. Appl. No. 17/305,421, filed Jul. 7, 2021, Pending.
E. J. Candes and M. B. Wakin, "An introduction to compressive sampling," Signal Processing Magazine, IEEE, vol. 25, No. 2, pp. 21-30,2008.
E. J. Candes and T. Tao, "Decoding by linear programming," Information Theory, IEEE Transactions on, vol. 51, No. 12, pp. 4203-4215, 2005.
O. Michailovich and D. Adam, "Phase unwrapping for 2-d blind deconvolution of ultrasound images," Medical Imaging, IEEE Transactions on, vol. 23, No. 1, pp. 7-25.
T. Taxt and G. V. Frolova, "Noise robust one-dimensional blind deconvolution of medical ultrasound images," Ultrasonics, Ferroelectrics, and Frequency Control, IEEE Transactions on, vol. 46, No. 2, pp. 291-299, 1999.
J. F. Synnevag, A. Austeng, and S. Holm, "Benefits of minimum-variance beamforming in medical ultrasound imaging," Ultrasonics, Ferroelectrics, andFrequency Control, IEEE Transactions on, vol. 56, No. 9, pp. 1868-1879, 2009.
S. Holm, J. Synnevag, and A. Austeng, "Capon beamforming for active ultrasound imaging systems," in Proc. IEEE, 13th DSP Workshop, 2009.
J. A. Mann and W. Walker, "A constrained adaptive beamformer for medical ultrasound: Initial results," in Ultrasonics Symposium, 2002. Proceedings. 2002 IEEE, vol. 2. IEEE, 2002, pp. 1807-1810.
I. K. Holfort, F. Gran, and J. A. Jensen, "Minimum variance beamforming for high frame-rate ultrasound imaging," in Ultrasonics Symposium,2007. IEEE. IEEE, 2007, pp. 1541-1544.
B. M. Asl and A. Mahloojifar, "Eigenspace-based minimum variance beamforming applied to medical ultrasound imaging," Ultrasonics, Ferroelectrics, and Frequency Control, IEEE Transactions on, vol. 57, No. 11, pp. 2381-2390, 2010.
M. Schiffner, T. Jansen, and G. Schmitz, "Compressed sensing for fast image acquisition in pulse-echo ultrasound," Biomedical Engineering/Biomedizinische Technik, vol. 57, No. SI-1 Track-B, pp. 192-195, 2012.
N. Wagner, Y. C. Eldar, A. Feuer, G. Danin, and Z. Friedman, "Xampling in ultrasound imaging," CoRR, vol. abs/1104.5327, 2011.
N. Wagner, Y. C. Eldar, A. Feuer, and Z. Friedman, "Compressed beamforming applied to b-mode ultrasound imaging," in Biomedical Imaging (ISBI), 2012 9th IEEE International Symposium on. IEEE, 2012, pp. 1080-1083.
P. Blomgren, G. Papanicolaou, and H. Zhao, "Super-resolution in time-reversal acoustics," The Journal of the Acoustical Society of America, vol. 111, No. 1, pp. 230-248, 2002.
A. J. Devaney, "Super-resolution processing of multi-static data using time reversal and music," 2000.
Y. Labyed and L. Huang, "Super-resolution ultrasound imaging using a phase-coherent music method with compensation for the phase response of transducer elements," Ultrasonics, Ferroelectrics, and Frequency Control, IEEE Transactions on, vol. 60, No. 6, pp. 1048-1060, 2013.
M.A. O'Reilly and K. Hynynen, "A super-resolution ultrasound method for brain vascular mapping," Medical physics, vol. 40, No. 11, p. 110701, 2013.
B. Cox and P. Beard, "Imaging techniques: Super-resolution ultrasound," Nature, vol. 527, No. 7579, pp. 451-452, 2015.
C. Errico, J. Pierre, S. Pezet, Y. Desailly, Z. Lenkei, O. Couture, and M. Tanter, "Ultrafast ultrasound localization microscopy for deep super-resolution vascular imaging," Nature, vol. 527, No. 7579, pp. 499-502, 2015.
T. Dertinger, R. Colyer, R. Vogel, J. Enderlein, and S. Weiss, "Achieving increased resolution and more pixels with superresolution optical fluctuation imaging (sofi)," Optics express, vol. 18, No. 18, pp. 18 875-18 885, 2010.
T. Taxt and R. Jirik, "Superresolution of ultrasound images using the first and second harmonic signal," Ultrasonics, Ferroelectrics, and Frequency Control, IEEE Transactions on, vol. 51, No. 2, pp. 163-175, 2004.
D. Kouame and M. Ploquin, "Super-resolution in medical imaging: An illustrative approach through ultrasound," in Biomedical Imaging: From Nano to Macro, 2009. ISBI'09. IEEE International Symposium on. IEEE, 2009, pp. 249-252.
G. Clement, J. Huttunen, and K. Hynynen, "Superresolution ultrasound imaging using back-projected reconstruction," The Journal of the Acoustical Society of America, vol. 118, No. 6, pp. 3953-3960, 2005.
J. N. Wright, "Image formation in diagnostic ultrasound," 1997.
J. W. Goodman, "Introduction to fourier optics," 2005.
T. Szabo, Diagnostic Ultrasound Imaging: Inside Out, ser. Academic Press series in biomedical engineering. Elsevier Academic Press, 2004. [Online]. Available https://books.google.com/books?id =-Fd1 Pkeh2TOC.
B. R. Hunt, "Super-resolution of imagery: understanding the basis for recovery of spatial frequencies beyond the diffraction limit," in Information, Decision and Control, 1999. IDC 99. Proceedings. 1999. IEEE, 1999, pp. 243-248.
E. J. Candes and C. Fernandez-Granda, "Towards a mathematical theory of super-resolution," CoRR, vol. abs/1203.5871, 2012.
B. E. Treeby, J. Jaros, A. P. Rendell, and B. Cox, "Modeling nonlinear ultrasound propagation in heterogeneous media with power law absorption using a k-space pseudospectral method," The Journal of the Acoustical Society of America, vol. 131, No. 6, pp. 4324-4336, 2012.

(56) References Cited

OTHER PUBLICATIONS

George, Swetha et al: "A novel ultrasound imaging technique for portable and high speed imaging" IEEE 13th International New Circuits and System Conference (NEWCAS). Jun. 7, 2015, pp. 1-4.
Apr. 19, 2016 International Search Report and Written Opinion in connection with International Application No. PCT/US2015/065722.
Mar. 5, 2018 International Search Report and Written Opinion in connection with International Application No. PCT/US2017/061501.
Charles J. Pavlin et al. "Advances in Ultrasound Biomicroscopy," Ultrasound in Medicine & Biology, vol. 26, No. 1, pp. 1-27, Feb. 2000.
Viola et al. "Time-Domain Optimized Near-Field Estimator for Ultrasound Imaging: Initial Development and Results", NIH Public Acess Author Manuscript, Jan. 2008.
Ellis et al., Super-Resolution Image Reconstruction With Reduced Computational Complexity, 2009 IEEE Ultrasonics Symposium Proceedings, p. 2351-2354.
Ellis et al., Super-Resolution Image Reconstruction Using Diffuse Source Models, NIH Public Acess Author Manuscript, Jun. 2010.
Yankelevsky et al., Component Based Modeling of Ultrasound Signals, Mar. 1, 2016.
AAPM/RSNA Physics Tutorial for Residents: Topics in US B-mode US: Basic Concepts and New Technology.
R. Kazys, L. Svilainis, and L. Mazeika, "Application of orthogonal ultrasonic signals and binaural processing for imaging of the environment", Ultrasonics, vol. 38, No. 18, p. 171175, Mar. 2000.
Parker, Kevin J. "Superresolution imaging of scatterers in ultrasound B-scan imaging, " The Journal of the Acoustical Society of America, 131, 4680-4689 (2012).
Jensen, J. A., "Deconvolution of ultrasound images" Ultrasonic Imaging, vol. 14, Issue 1, pp. 1-15, 1992.
Alam, S. K., Ophir, J., Cespedes, I., and Varghese T. "A deconvolution filter for improvement of time delay estimation in elastography" IEEE Trans. Ultrason. Ferroelectr. Freq. Control 45, pp. 1565-1572 (1998).
Michailovich, O. and Adam, D. "Phase unwrapping for 2-D blind deconvolution of ultrasound images" IEEE Trans. Med Imaging, 2004, 23, pp. 7-25.
Shin, H. C., Prager, R., Gomersall, H., Kingsbury, N., Treece, G., and Gee, A "Estimation of average speed of sound using devconvolution of medical ultrasound data" Ultrasound Med. Biol. 2010, 36, pp. 623-636.
Synnevag, J. F.; Austeng, A.; Holm, S., "Minimum variance adaptive beamforning applied to medical ultrasound imaging" Ultrasonics Symposium, 2005 IEEE, vol. 2, pp. 1199-1202.
Asl, B.M.; Mahloojifar, A. "Minimum variance beamforming combined with adaptive coherence weighting applied to medical ultrasound imaging" Ultrasonics, Ferroelectrics, and Frequency Control, IEEE Transactions on, vol. 56, No. 9, pp. 1923-1931, Sep. 2009.
Asl, B.M.; Mahloojifar, A. "Eigenspace-based minimum variance beamforning applied to medical ultrasound imaging" Ultrasonics, Ferroelectrics, and Frequency Control, IEEE Transactions on I vol. 57, No. II, pp. 2381,2390, Nov. 2010.
T. Chemyakova and Y. C. Eldar "Fourier Domain Beamforning: The Path to Compressed Ultrasound Imaging" IEEE Transactions on Ultrasonics, Ferroelectronics, and Frequency Control, vol. 61,issue 8, pp. 1252-1267, Jul. 2014.
N. Wagner, Y. C. Eldar and Z. Friedman "Compressed Beamforming in Ultrasound Imaging" IEEE Transactions on Signal Processing, vol. 60, issue 9, p. 46434657, Sep. 2012.
H. Liebgott, R. Prost, and D. Friboulet "Prebeamformed rf signal reconstruction in medical ultrasound using compressivesensing" Ultrasonics, 2012, 53, 525-533.
D. Friboulet, H. Liebgott, and R. Prost, "Compressive sensing for raw rf signals reconstruction in ultrasound" IEEE International Ultrasonics Symposium, 2010, 367-370.

Michailovich, 0. and Adam, D. "Phase unwrapping for 2-D blind deconvolution of ultrasound images" IEEE Trans. Med Imaging, 2004, 23, pp. 7-25.
Shin, H. C., Prager, R., Gomersall, H., Kingsbury, N., Treece, G., and Gee, A "Estimation of average speed of sound using deconvolution of medical ultrasound data" Ultrasound Med. Biol. 2010, 36, pp. 623-636.
Synnevag, J.-F.; Austeng, A.; Holm, S., "Minimum variance adaptive beamforrning applied to medical ultrasound imaging" Ultrasonics Symposium, 2005 IEEE, vol. 2, pp. 1199-1202.
Asl, B.M.; Mahloojifar, A. "Eigenspace-based minimum variance beamforrning applied to medical ultrasound imaging" Ultrasonics, Ferroelectrics, and Frequency Control, IEEE Transactions on I vol. 57, No. 11, pp. 2381,2390, Nov. 2010.
T. Chemyakova and Y. C. Eldar "Fourier Domain Beamforrning: The Path to Compressed Ultrasound Imaging" IEEE Transactions on Ultrasonics, Ferroelectronics, and Frequency Control, vol. 61,issue 8, pp. 1252-1267, Jul. 2014.
N. Wagner, Y. C. Eldar and Z. Friedman "Compressed Beamforming in Ultrasound Imaging" IEEE Transactions on Signal Processing, vol. 60, issue 9, p. 46434657, Sep. 2012.
C. Quinsac, A. Basarab. J. M. Girault, and D. Kouam "Compressed sensing of ultrasound images: sampling of spatial and frequency domains." IEEE Workshop on Signal Processing Systems, 2010, 231-236.
C. Quinsac, N. Dobigeon, D. Kouam, and J. Toumeret "30 compressed sensing ultrasound imaging" IEEE International Ultrasonics Symposium Proceedings, 2010, 363-366.
R. Turf Y. C. Eldar, and Z. Friedman "Innovation rate sampling of pulse streams with application to ultrasound imaging" IEEE transactions on Signal Processing, 2011, vol. 59, No. 4, pp. 1827-1842.
S. Campbell "A Short History of Sonography in Obstetricsand Gynecology" Facts Views Vis Obgyn 2013, v.5(3): pp. 213-229.
F. J. Fry, J. E. Barger "Acoustical properties of the human skull" J. Acoust. Soc. Am. 63, 1576 (1978).
P. J. White, G.T. Clement, K. Hynynen "longitudinal and shear mode ultrasound propagation in human skull bone" Ultrasound in Medicine & Biology, vol. 32, Issue 7, Jul. 2006, pp. 1085-1096.
N. Petridou, M. Italiaander, B. L. van de Bank, J.C. W. Siero, P. R. Iuijten and D. W. J. Klomp "Pushing the limits of high-resolution functional MRI using a simple high-density multielement coil design" NHR in Biomedicine, ISSN 0952-3480, Jan. 2013, vol. 26, Issue 1, pp. 65-73.
Schmutzhard, S.; Jung, A.; Hlawatsch, F. "Minimum variance estimation for the sparse signal in noise model" Information Theory Proceedings (ISIT), 2011 IEEE International Symposium on, pp. 124-128, Jul. 31, 2011-Aug. 5, 2011.
Juhwan Yoo; Becker, S.; Monge, M.; Loh, M.; Candes, E.; Emami-Neyestanak., A "Design and implementation of a fully integrated compressed-sensing signal acquisition system" Acoustics, Speech and Signal Processing (ICASSP), 2012 IEEE International Conference on, pp. 5325-5328, Mar. 25-30, 2012.
J. W. Goodman, Statistical Optics., Wiley-Interscience, New York, 1985.
Burckhardt, C.B. "Speckle in ultrasound B-mode scans" Sonics and Ultrasonics, IEEE Transactions on , vol. 25, No. 1, pp. 1-6, Jan. 1978.
Ouyang, G. "Laser speckle reduction based on angular diversity induced by Piezoelectric Benders" Journal of European optical Society-Rapid Publications, ISSN 1990-2573, 2013, vol. 8, pp. 4.
M. N. Akram, Z. Tong, G. Ouyang, X. Chen, and V. Kartashov "Laser speckle reduction due to spatial and angular diversity introduced by fast scanning micromirror" Appl. Optics 2010, 49(17), 3297-3304.
J. A. Jensen "Field: a program for simulating ultrasound systems" in 10th Nordicbaltic Conference on Biomedical Imaging, Supplement 1, Part 1, vol. 34, 1996, pp. 351-353.
T. Hastie, R. Iibshirani, and J. Friedman, The Elements of Statistical Learning, 2nd ed. New York: Springer, 2009.
R. Tibshirani "Regression shrinkage and selection via the lasso" J. Roy. Stat. Soc. 8, vol. 58, pp. 267-288, 1996.

(56) References Cited

OTHER PUBLICATIONS

M. W. Mahoney "Randomized algorithms for matrices and data" Foundations and Trends in Machine Learn., vol. 3, No. 2. pp. 123-224, 2011.
K. L. Clarkson and D. P. Woodruff "Low rank approximation and regression in input sparsity time" Proc. Symp. Theory Computing, Jun. 1-4, 2013, pp. 81-90.
K. Slavakis, G. B. Giannakis, and G. Mateos "Modeling and optimization for Big Data analytics" IEEE Signal processing Magazine, vol. 31, No. 5, pp. 18-31, Sep. 2014.
V. M. Patel, H. V. Nguyen, and R. Vidal "Latent space sparse subspace clustering" Proc. of Intl. Conf. Computer Vision, Sydney: Australia, 201, 225-232.
S. Shalev-Shwartz "Online learning and online convex optimization" Foundations and Trends in Machine Learning, vol. 4, No. 2, pp. 107-194, 2012.
H. Mardani, G. Mateos, and G. B. Giannakis "Dynamic anomalography: Tracking network anomalies via sparsity and lowrank" IEEE Journal of Sel. Topics in Signal Processing, vol. 8, Feb. 2013.
M. Mardani, G. Mateos, and G. B. Giannakis "Decentralized sparsity regularized rank minimization: Algorithms and applications" IEEE Trans. on Signal Processing, vol. 61. pp. 5374-5388, Nov. 2013.
G. Mateos, J. A. Bazerque, and G. B. Giannakis "Distributed sparse linear regression" IEEE Trans. Signal Processing, vol. 58, No. 10, pp. 5262-5276, Oct. 2010.
G. Mateos, I. D. Schizas, and G. B. Giannakis "Distributed recursive least-squares for consensus-based in network adaptive estimation" IEEE Transactions on Signal Processing, 2009, vol. 57, No. 11, pp. 4583-4588.
K. Slavakis, S . .J. Kim, G. Mateos, and G. B. Giannakis "Stochastic approximation vis-a-vis online learning for Big Data," IEEE Signal Processing Magazine, vol. 31, No. 6, pp. 124-129, Nov. 2014.
F. Bensaali, A. Arnira, .R. Sotudeh "Floating point matrix product on FPGA" Proc. IEEE/ACS Int. Conf. on Computer Systems and Applications, pp. 466-473, 2007.
C.Y. Lin, H.K.-H. So, P.H. Leong "A model for matrix multiplication performance on FPGAs" Proc. International Conference on Field Programmable Logic and Applications, pp. 305-310, Sep. 2011.
J. Fowers, K. Ovtcharov "A High Memory Bandwidth FPGA Accelerator for Sparse Matrix Vector Multiplication" Proc. IEEE 22nd International Symposium on Field-Programmable Custom Computing Machines, pp. 36-43, May 2014.
Z. Jovanovic, V. Milutinovic "FPGA accelerator for floating point matrix multiplication" IET Computers & Digital Techniques, 2012, 6(4): 249-256.
Synnev*ag et al. Adaptive Beamforming Applied to Medical Ultrasound Imaging, IEEE transactions on ultrasonics, ferroelectrics, and frequency control, vol. 54, No. 8, 1606-1613, Aug. 2007 (Year: 2007).

\* cited by examiner

ULTRASOUND SYSTEM FOR HIGH-SPEED AND HIGH RESOLUTION IMAGING APPLICATIONS

This application is a divisional application of U.S. application Ser. No. 15/529,174, filed May 24, 2017, which is national stage of International Patent Application No. PCT/US2015/065722, filed Dec. 15, 2015, which claims priority to provisional Application No. 62/094,654, filed Dec. 19, 2014. The entirety of the aforementioned applications is incorporated herein by reference.

FIELD

This disclosure relates generally to ultrasound apparatuses and methods for obtaining an ultrasound image, and more particularly, to ultrasound apparatuses and methods for obtaining a high-speed and high resolution ultrasound image.

BACKGROUND

Widely used medical imaging modalities can be broadly classified into three categories based on the method of irradiation: (1) X-ray imaging; (2) radio frequency (RF) electromagnetic wave imaging; and (3) acoustic pressure wave imaging. With respect to the first method, capturing X-rays leads to computed tomography (CT) imaging. With respect to the second method, excited water molecules emit RF waves, whose spatial quantities can be counted in magnetic resonance imaging (MRI). Moreover, with respect to the third method, the reflection of acoustic pressure waves, typically at high audio frequencies, gives rise to ultrasound (US) imaging.

In addition to the field of medicine, these three imaging techniques are invaluable for their non-invasive diagnostic contribution to geology, material testing, and other disciplines. Moreover, each of the three imaging techniques has its own advantages and limitations. For example, CT imaging has the advantage of being able to yield high-resolution pictures at relatively low cost. However, X-rays must be carefully administered because of detrimental cumulative effects. Thus, proper CT imaging uses the minimum amount of X-ray radiation necessary to obtain a useful picture, with due consideration to lifetime dosage limitations. In contrast, MRI is regarded as a safer alternative. However, maintaining MRI machines is considerably more expensive compared to CT machines. Thus, the relatively higher cost associated with MRI prohibits its use in casual diagnostics.

Ultrasound imaging is both safe and relatively inexpensive to use, and can yield images with comparable quality as CT and MRI in certain imaging scenarios such as subcutaneous soft tissue imaging. For example, using ultrasound is the preferred way of imaging an unborn fetus because of its non-ionizing radiation and accessibility. However, conventional ultrasound imaging algorithms and sensor array geometries, as shown in FIG. 8, limit the overall frame rate and image quality defined in terms of resolution and signal-to-noise (SNR) ratio [1]. For example, the frame rate of a conventional B-mode (or 2D imaging) ultrasound system, where the images are generated one scan line at the time, is bottlenecked by the acoustic waveform propagation times [2]. In addition to the limited image acquisition speed, conventional ultrasound systems suffer from sidelobe artifacts due to the focusing nature of these imaging systems [1]. Another important limitation of conventional ultrasound systems is speckle noise arising from the coherent and unchanging illumination of the target medium [3]. Both speckle noise and sidelobes significantly limit imaging quality and resolution of conventional ultrasound systems.

A variety of methods on improving the image quality, resolution, and speed of conventional ultrasound systems have been proposed and experimentally verified over the last five decades. These methods can be broadly classified into three categories. The first category is focused on adjusting the shape of the ultrasonic excitation pulse to increase its effective bandwidth and applying an inverse filter on the received signal (so called de-convolution) to improve image quality [3]-[7]. The second group comprises methods based on improving the so-called beamforming function at the receive side to minimize imaging error [8]-[10]. The third and more recent category is focused on image data post-processing to improve the resolution and image quality and reduce complexity by taking advantage of sparsity of typical ultrasound image [11]-[17].

Even though successful in improving the image quality and resolution, these methods require significant hardware modifications and increase in cost/complexity. For example, in all of these categories the core of the ultrasound sensing array, as shown in FIG. 8, remains basically unchanged. That is, each element of the array remains equipped with a complex chain of analog signal acquisition and data conversion blocks (digital-to-analog converter and power amplifier for acoustic pulse generation, as well as low-noise amplifier and analog-to-digital converter (ADC) for echo receiving), which does not favor portable battery-operated implementations and further scaling to larger arrays.

Therefore, there is a need for an ultrasound imaging system where the hardware complexity is reduced and the speed of operation and the image quality are increased.

Two lists of citation to references is included at the end of this disclosure, and the disclosure includes numbers in parenthesis that refer to the citations in Reference List A. Reference List B includes additional citations. All of the cited references are hereby incorporated by reference in this disclosure.

SUMMARY

An object of the present disclosure is to provide an ultrasound imaging system and method.

In general, in one aspect, the present disclosure includes an ultrasound system including an array of ultrasound transducer elements that send ultrasound energy into an object when energized for respective transmission time periods and provide responses to ultrasound energy emitted from the object for respective reception time periods, a reception modulation circuit modulating the responses with irregular sequences of modulation coefficients, a combiner circuit combining the modulated responses, and an image reconstruction processor configured to computer-process the combined modulated responses into one or more images of the object.

The ultrasound imaging system may further include one or more of the following features. The combiner circuit may be configured to combine the modulated responses in the analog domain. The combiner circuit may include at least two combiner channels each combining a respective subset of the responses. The reception modulation circuit may be configured to modulate the response with a sequence of pseudo-random modulation coefficients. The reception modulation circuit may be configured to modulate the response with coefficients related to columns of Hadamard matrices. The system may include a transmission modulation circuit configured to select for energizing in each transmission period only plural-element subsets of the transducer elements that differ between transmission time periods. The modulation circuit may be configured to energize only pseudo-randomly selected different subsets of the transducer elements for different transmission time periods. The modulation circuit may be configured to modulate the responses in the analog domain with waveforms of positive and negative levels. The combiner circuit may include at least one amplifier having a positive input receiving the portions of the responses modulated with the positive levels and a negative input receiving the portions of the responses modulated with the negative levels of the modulating waveforms. The reconstruction processor may be configured to apply an imaging matrix to the combined modulated responses to thereby generate the one or more images of the object.

In general, in another aspect, the present disclosure includes an ultrasound imaging system that includes a multi-element set of ultrasound transducer elements, an excitation pulse generator providing a succession of excitation pulses, a receiving switch matrix modulating echoes received by the transducer elements with an essentially random sequence of modulation coefficients, a circuit summing the modulated echoes in the analog domain, and an image reconstruction processor configured to computer-process the summed modulated echoes into one or more images of the object.

The ultrasound imaging system may further include one or more of the following features. The receiving switch matrix may be configured to modulate the echoes with modulating waveforms having irregular periods. The modulating waveforms may include waveforms of a succession of positive and negative levels. The system may include a differential charge amplifier, and the echoes modulated with the positive levels may be supplied to a positive input and the echoes modulated with the negative levels may be supplied to a negative input of the differential amplifier. The image reconstruction processor may be configured to apply an image matrix to the summed modulated echoes to generate an image of the object. The image matrix may be selected to relate summed echoes from a known object to an expected image of the object generated with the image reconstruction processor. The system may include an analog-to-digital converter (ADC) converting the summed echoes into a digital sequence supplied to the image reconstruction processor. The system may include a transmission switch matrix transmitting each excitation pulse only to a respective, essentially randomly selected subset of the elements in the set.

DETAILED DESCRIPTION

This disclosure describes ultrasound imaging systems and methods. In describing examples and exemplary embodiments shown in the Figures, specific terminology may be employed for the sake of clarity. However, this disclosure should not be limited to the specific terminology so selected, and it should be understood that each specific element includes all technical equivalents that may operate in a similar manner.

Figure 8:
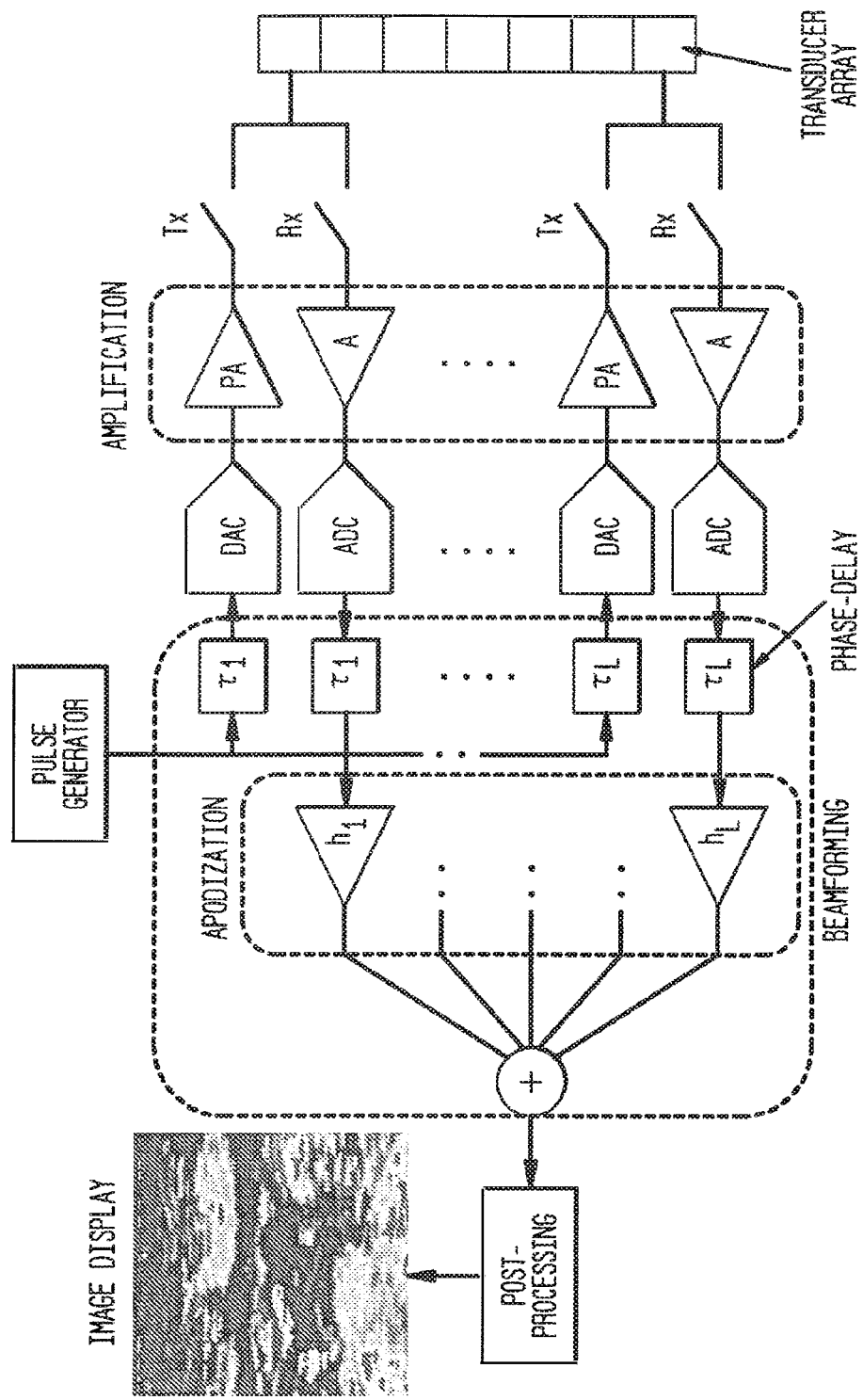
FIG. 8 shows a block diagram of a conventional ultrasound imaging system.

FIG. 8 illustrates an example of a conventional ultrasound system. In general, early B-mode (or 2D imaging) ultrasound systems (e.g., ultrasound systems developed in the 1960s) were entirely analog, including the beamforming function that performed the delay-and-sum (or electronic focusing) operation. Because of advances with digital computers, the analog scanning stages of the early B-mode ultrasound systems were replaced by digital components which improved image reproducibility [18]. FIG. 8 shows that for each transducer, an individual excitation pulse is generated, and the echo signal received from each point is received in a corresponding chain including an analog-to-digital converter (ADC) and an amplifier.

FIG. 8 additionally shows that the early B-mode ultrasound systems create an image by measuring the echo signal power from one point at a time, while ignoring contributions from point scatterers that are off the focal axis. This results in the loss of phase information across the elements of the array after the beamforming function. Accordingly, traditional ultrasound systems, such as the system of FIG. 8, can be described as incoherent imaging systems.

Additionally, in general, in conventional ultrasound systems, such as the system of FIG. 8, the spatial resolution is theoretically bounded by Abbe's diffraction limit ($D_{Abbe}=\lambda/2NA$), even in the absence of system noise, where $\lambda$ is the wavelength of the excitation pulse, and NA is the numerical aperture of the imaging system. With this theoretical limit, spatial resolution in ultrasound systems may be improved through the use of higher frequency ultrasonic waves, larger arrays, and/or use of some a priori knowledge about the imaged signal (such as sparsity).

In addition to Abbe's diffraction limit, other system parameters including, at least, noise and signal power play an important role in limiting imaging resolution. Moreover, physical parameters of the transducer array and imaging scenario set fundamental limits on ultrasound systems.

This specification addresses ways to take advantage of the coherence of the received echo signals and to utilize the additional phase information to improve imaging resolution dramatically with minimal or at least lesser need for additional electronics resources.

Figure 1:
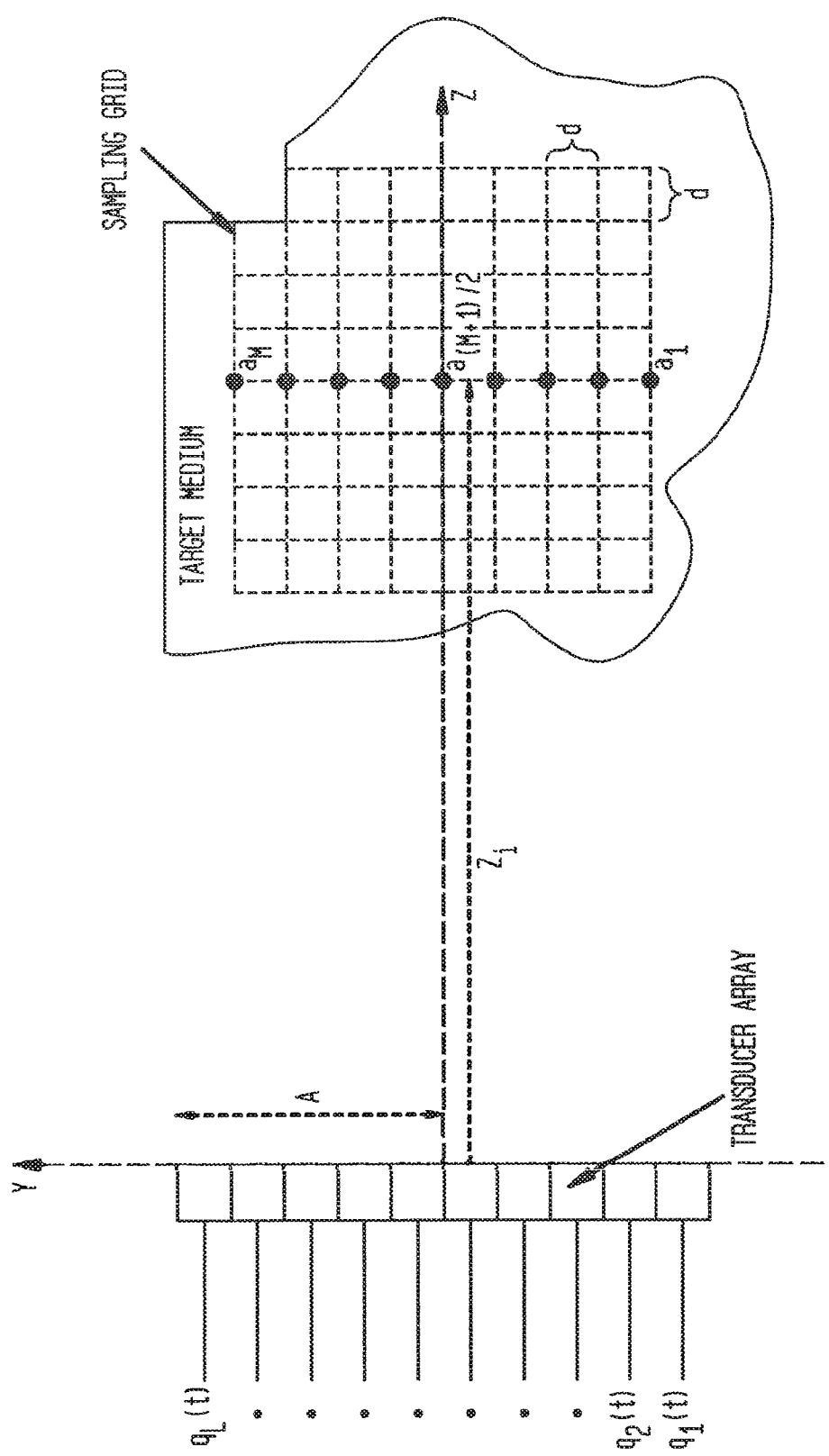
FIG. 1 shows a model of an ultrasound imaging system used for calculating Cramer-Rao Lower Bound.

FIG. 1 illustrates an ultrasound imaging systems including a linear transducer array of L transducer elements with spacing $\lambda/2$ illuminating a target medium located along a central axis of the array at a distance $Z_i$. FIG. 1 shows that the target medium may be uniformly sampled with a spacing d. During a single observation the array transmits a finite length plane wave excitation pulse s(t) with wavelength $\lambda$ and captures data from each sampling point with a reflectance coefficient $a_j$. The set of all reflectance coefficients represented as vector $a=[a_1\ a_2\ \ldots\ a_M]^T$ is a deterministic vector parameter to be estimated, which represents the final ultrasound image of a target medium.

In some embodiments, received signals $q_k(t)$ from the transducer elements (i.e., RF data) are combined into a single channel Q(t) by means of a linear function, H (i.e., the beamforming function). In alternative embodiments, such as the embodiment of FIG. 1, for the purpose of estimation error and resolution analysis the individual received signals $q_k(t)$ may each be available to the image reconstruction (or estimation) algorithm. In this manner, the effects of the linear function H on estimation error may be analyzed.

In one embodiment, such as the embodiment of FIG. 1, the fundamental limits set by the physical parameters of the transducer array and the imaging scenario may be determined by finding a Cramer-Rao Lower Bound (CRLB) for estimation error. In the embodiment of FIG. 1, a contributor to error may be point scatterers in the azimuthal neighborhood (along y-axis). In some embodiments, point scatterers at different range distances Z may also contribute to error. However, in the embodiment of FIG. 1, point scatters at different range distances Z may not be considered, because the propagation time difference between two scatterers along the y-axis is orders of magnitude shorter than the propagation time difference between two scatterers along z-axis due to the far-field imaging assumption (i.e., distance $Z_i$ is much greater than the array's aperture).

After a single plane-wave excitation s(t) transmitted by the array, the received sampled signal at the $k^{th}$ element of the transducer array may be equal to, $$q_k(nT_s)=a_1 s(nT_s-t_{1k})+\ldots+a_M s(nT_s-t_{Mk})+w(nT_s)=s(nT_s;a)+w(nT_s) \quad (1)$$

where $w(nT_s)$ are the samples of a zero-mean additive white Gaussian (AWG) noise, and $t_{jk}$ is the propagation time from the scatterer at $(z_i, y_j)$ with reflectance coefficient $a_j$ to the $k^{th}$ transducer element.

Equation (2), defined below, may be used in connection with the ultrasound imaging system of FIG. 1 in order to derive the CRLB for the variance of the estimation error of reflectance parameters $var(\hat{a}_j-a_j)$. In Equation (2), eSNR represents a Signal-to-Noise ratio (SNR) received by one element of the array, L is the number of array elements, p is the number of independent observations of the imaged tissue, d is the sampling grid spacing, and $BW_\%$ is the fractional bandwidth of the excitation pulse defined as the ratio of its effective bandwidth and its center frequency $f_0$. Additionally, wavelength $\lambda$ corresponds to the center frequency $f_0$ as $\lambda=v_s/f_0$, where $v_s$ is the speed of sound in the imaging medium.

$$\mathrm{var}(\hat{a}_j - a_j) \geq \frac{1}{BW_\% \cdot L \cdot p \cdot eSNR} \frac{D_{Abbe}}{d} \quad (2)$$

From the CRLB of the reflectance parameters, the fundamental limit on image resolution d may be obtained, which may be shown in Equation (3) below. In Equation (3), CR is the contrast resolution (or peak imaging SNR) required by the imaging application.

$$d(CR) \geq \frac{CR}{L \cdot p \cdot eSNR} \frac{D_{Abbe}}{BW_\%} \quad (3)$$

Equation (3) shows that it is possible to capture ultrasound images at a sub-wavelength resolution (below Abbe's diffraction limit) although at the expense of image quality (or reduced CR). Additionally, for the same imaging system parameters (CR, NA, and $BW_\%$), the imaging resolution d can be improved by capturing more images to "average out" the system noise and increase the total SNR received by the array. The following scenario illustrates the significance of this result.

For example, if $f_0$=600 kHz, $BW_\%$=0.5, L=: 16, NA, =0.2 (corresponding to an imaging depth of 5 cm), eSNR=15 dB and p=10, then the Abbe's diffraction-limited resolution is about $2.5\lambda$ (6.2 mm). At the same time, the resolution limit from Equation (3) is equal to $0.03\lambda$ (or 78 µm) for a CR of 15 dB. Based on this, an ultrasound system that can preserve all the information present in RF data should be, at least theoretically, capable of imaging with resolutions exceeding that of modem MRI machines (~0.6 mm in [21]) at only a fraction of the equipment cost and imaging time [22]. For example, it has been shown that an ultrasonic pulse at 600 kHz can penetrate the human skull without significant attenuation [19]-[20] The embodiment of FIG. 1 and corresponding equations show that the ultrasound system may be configured to preserve the information present in the RF data and further may be configured to generate an image with increased resolution at an increased speed with a lower cost of ultrasound system equipment.

In the embodiment of FIG. 1, Equation (3) represents a fundamental limit on the resolution of the ultrasound imaging system when estimated reflectance parameters are non-zero and no a priori knowledge about their statistics is available. In alternative embodiments, where additional information about the estimation parameters, including, but not limited to, sparsity in some domain, may be available, there may be a further decrease in estimation error and improvements in resolution.

The fundamental limit on imaging resolution previously discussed was derived assuming that signals from individual transducer elements are available. In most practical applications this is not realistic due to the sheer volume of data (which may exceed GB/s). Therefore, in some embodiments, the RF data may be combined by means of a linear transform function H or beamforming function, where the channels are phase-delayed, weighted with an apodization window, and summed up into a single channel Q(t). In general, the phase-delay operation can be ignored since it is a reversible operation, with no effect on the information content and estimation error. Moreover, since the apodization window of traditional ultrasound imaging systems is usually a low-pass spatial filter with filter coefficients that do not change over different time samples, linear transformation function H can be described as a linear time-invariant (LTI) transform. As such, the linear transformation function H may cause loss of information at higher spatial frequencies, illustrated by a relatively poor resolution limit of $2$-$3\lambda$ in traditional ultrasound imaging systems.

In addition to reduced spatial resolution due to the focusing nature, another problem with traditional ultrasound system images is sidelobe artifacts, which appear as extraneous reflections from out-of-focus scatterers that are incorrectly interpreted as the signal along the main focusing axis

[1]. In the embodiments of the present disclosure, sidelobe artifacts may be significantly reduced and even eliminated.

Returning the information obtained in RF data, there may be conditions that linear transformation function H must satisfy in order to preserve all the information available in RF data and not affect the estimation error. First, since far-field imaging may be assumed, the azimuthal bandwidth (bandwidth along the y-axis) may be reduced 1/NA times with respect to the range bandwidth (or z-axis). Therefore, since the signal samples across the elements of the array at any given time instance are oversampled by a factor of 1/NA, they are highly correlated, occupying only a fraction of the available bandwidth. Accordingly, in some embodiments, one way of preserving all or most of the information is to spread the information across the frequency range defined by the sampling frequency ($f_s$). As long as the number of transducer elements L is smaller than 1/NA, information from each of the elements can be modulated to one of the non-overlapping spectral channels and no loss of information is expected. Because linear transformation function H is linear, it must be time-varying to generate frequencies that are not present at its input.

Based on the discussion of FIGS. 8 and 1 and Equations (1)-(3), an ultrasound imaging array equipped with a linear time-varying (LTV) beamforming function may be capable of achieving a sub-wavelength imaging resolution, where the resolution can be readily traded for image quality. Accordingly, embodiments of the present disclosure implement an LTV beam-forming function, with a suitable excitation waveform, in an efficient manner and at affordable hardware costs.

For example, in some embodiments, a random modulation pre-integration (RMPI) function [23], where linear transformation function H is implemented with mutually orthogonal pseudo-random vectors of 1's and −1's, may be configured to perform a spectral spreading operation. This enables simplification of the echo receive hardware to a switch matrix that changes the polarity of signal samples from individual elements. Additionally, this enables simplification of the hardware such that only one summation amplifier and one ADC that operates at speeds comparable to the speed of one ADC in traditional ultrasound arrays may be necessary.

In embodiments of the present disclosure, the beamforming function of the ultrasound imaging system may be time-varying over different time and spatial samples, uniformly spreading the information from different point scatterers over each of the output signal samples (i.e., all point scatterers in the imaged medium are treated equally as opposed to traditional methods that focus at one scatterer at a time). This may result in a reconstructed ultrasound image that may exhibit reduced or even eliminated sidelobe artifacts.

Embodiments of the present disclosure additionally provide improvements with respect to speckle noise. In general, speckle noise arises from point scatterers that do not coincide with sampling grid points, an unavoidable issue in practical media. Speckles typically appear as a fixed (although unpredictable) constructive/destructive interference pattern due to coherent and unchanging illumination of the target medium [24]-[25]. The appearance of speckle noise can be reduced by averaging multiple images of the same target at different illumination angles (i.e, an incoherent sum of multiple coherent images) [26]-[27]. In traditional ultrasound imaging systems, where the target medium is usually illuminated with the same excitation waveform for one B-scan line at the time, the impossibility of repeated observations means speckle noise is a significant source of error. However, in embodiments of the present disclosure, incoherent observations of coherent images can be readily implemented by selecting a random subset of array elements during a single target illumination, where the waveforms are transmitted with the same phase. No additional hardware is necessary because this random selection can be implemented with the same switch matrix used for beamforming.

Figure 2:
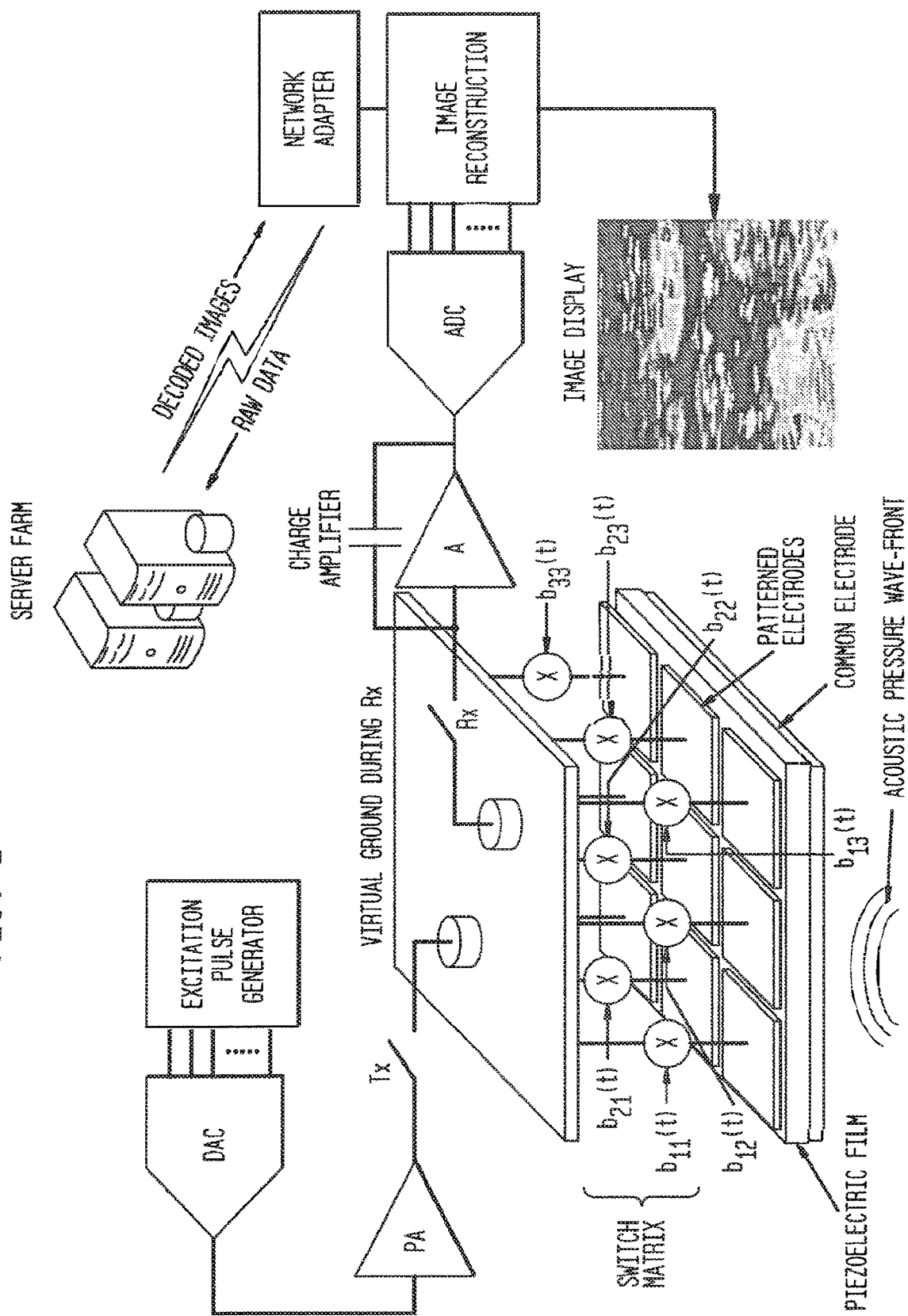
FIG. 2 shows an ultrasound system according to an embodiment of the present disclosure.

Turning now to FIG. 2, an ultrasound imaging system is illustrated according to an embodiment of the present disclosure. In general, FIG. 2 shows that received echo signals from the transducer elements, which may be located on the identified piezoelectric film, may be modulated by an appropriate pseudo-random sequence and then summed up in the analog domain, before they are passed through a single low-noise amplifier and ADC. The excitation pulse ($T_x$) may be simultaneously provided to all transducer elements selected for target illumination. As such, embodiments of the present disclosure may reduce the number of analog channels in the imaging system (including low-noise amplifier, power amplifier, ADC, and DAC) from one per array element to exactly one for the entire array. This hardware simplification indicates a total complexity and power reduction by a factor of L (typically 64-128), crucial in further developments of next generation battery-operated and portable US imaging systems. Furthermore, array geometries are no longer cost-limited to linear arrays containing hundreds of elements. Instead, full 2D arrays for 3D imaging may be economically produced containing several thousand elements. In addition to scalability, the disclosed embodiment also processes images using unfocused signals received from whole-medium irradiation. Thus, the embodiments of the present disclosure may be able to acquire the whole-medium image using a single, pulsed transmission. This provides for a drastic acquisition time speed up compared to conventional B-mode US imaging. In addition, since it can readily trade imaging speed for image quality, embodiments of the present disclosure provide imaging resolutions that may be close to the fundamental resolution limit, which is orders of magnitude higher than typical resolution of conventional ultrasound systems (e.g., ~0.1 mm vs. several millimeters) and comparable to that of modern MRI machines. These features may create new application opportunities such as 3D real-time heart imaging, deep tissue imaging, and even transcranial brain imaging, which were not previously possible or practical with traditional ultrasound systems. Moreover, because embodiments of the present disclosure use new computations for image reconstruction, there may be a substantially lower complexity and cost of front-end electronics. Therefore, when coupled with modern mobile platforms, including, but not limited to, tablets and smart phones, embodiments of the present disclosure may become genuinely portable.

More particularly, FIG. 2 illustrates a block schematic of an ultrasound system according to an embodiment of the present disclosure. As illustrated in FIG. 2, the system may include a 2D transducer array that may be fabricated as a piezoelectric film (such as PVDF) sandwiched between a grounded common electrode on one side and patterned electrodes on the other. The size of the patterned electrodes (~λ/2 squared) determines the size of one transducer element.

The size of the transducer array may be any size known to those skilled in the art. For example, in one embodiment, a small size transducer array consisting of 8×8 transducer elements with silver-coated patterned electrodes each with the size of 1.24 mm2 (corresponding to 600 kHz excitation frequency) may be procured from a piezoelectric film supplier. The transducer array may be bonded to a printed integrated circuit board with a conductive epoxy for mechanical support and interface to readout/driver electronics.

Figure 3:
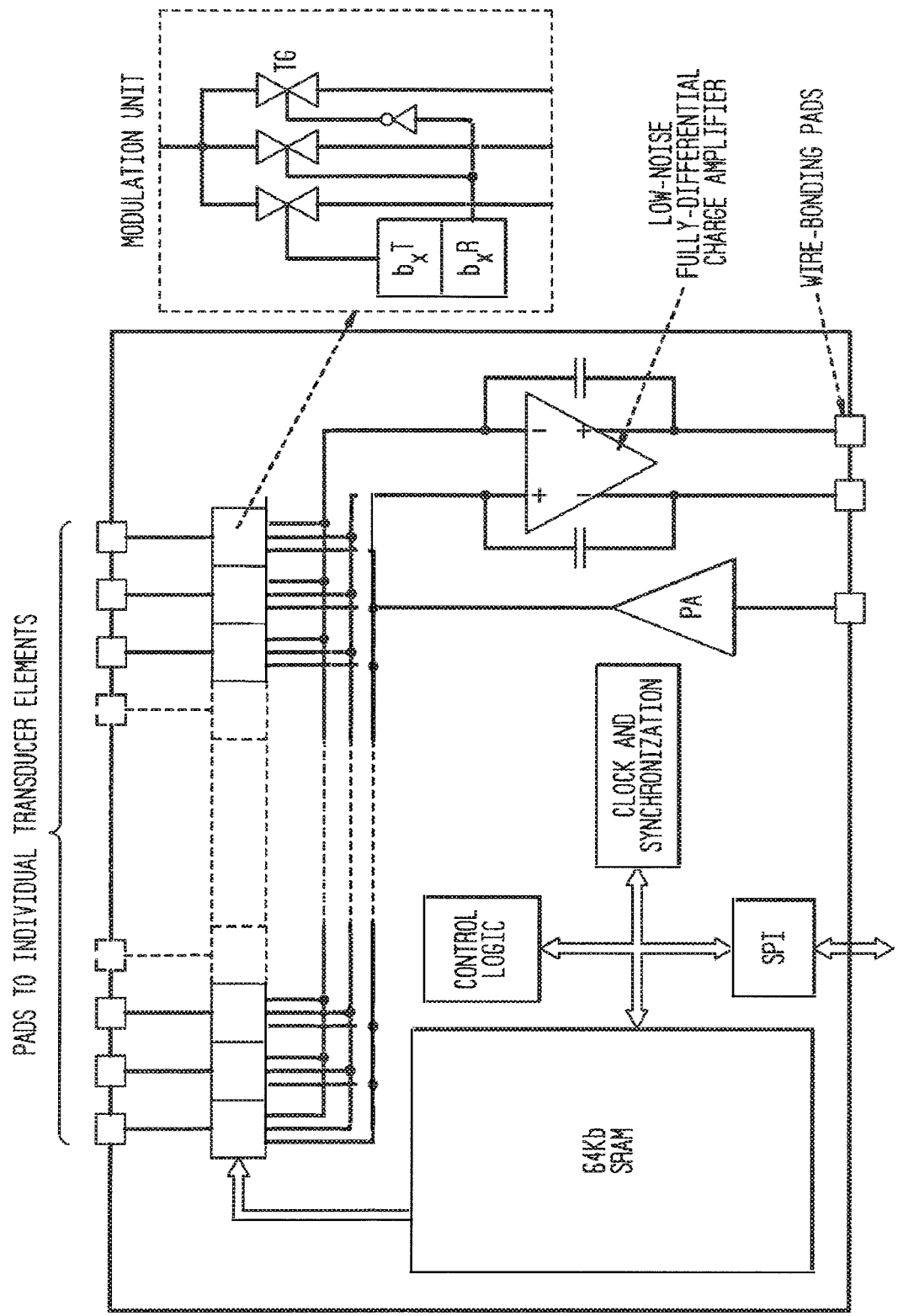
FIG. 3 shows a block diagram of an integrated circuit, according to an embodiment of the present disclosure.

FIG. 3 illustrates a block diagram of an integrated circuit according to an embodiment of the present disclosure. As illustrated in FIG. 3, the integrated circuit may include a memory block SRAM for modulation sequence storage, an on-chip low-noise charge amplifier, and power amplifier PA, control and synchronization logic including a clock, as well as an SPI interface for an off-chip access to the memory block. The integrated circuit may be designed and fabricated in any manner known to those skilled in the art. For example, in some embodiments the integrated circuit may be designed and fabricated via a high-voltage CMOS process, such as a 0.5 µm process.

FIG. 3 illustrates that the integrated circuit may additionally include a switch matrix. The switch matrix may be any device known to those skilled in the art including a set of devices for carrying out requisite switching with respect to each of the transducer elements on the transducer array. For example, in the embodiment of FIGS. 2 and 3, the switch matrix may include a plurality of modulation units. Each modulation unit may correspond to one of the transducer elements. The modulation units may each contain one transmission gate (TG) for the Tx phase and two TGs for the Rx phase. The TGs may be controlled by the modulation coefficients bTx and bRx, which are retrieved from a main memory block SRAM and temporarily stored in a small size (2-bit) memory buffer of the modulation unit within one sampling period (~200 ns).

During the excitation pulse transmission phase (Tx), an excitation pulse from the excitation pulse generator (FIG. 2) may first be converted to an analog signal (DAC) and amplified in a power amplifier (PA). The output from the PA may then be modulated by a modulation signal with modulation coefficients $b_{ij}(t)$, which may be constant during the entire length of the excitation pulse. In some embodiments, the modulation coefficients may be either 1 or −1. Alternatively, in some embodiments, such as the embodiment of FIG. 2, the modulation coefficients may be equal to either 1 or 0, which may be implemented as a switch matrix and fed to a subset of transducer elements. That is, in the embodiment of FIG. 2, a pseudo-randomly selected subset of transducer elements may be an array selected by modulation coefficients of zero and plus unity values, where a zero value means that a respective transducer element is not energized for a given transmission time period, and a plus unity value means the element is energized for that transmission time interval, and where the array of (0, 1) values is selected with some degree of randomness from one transmission time interval to another, such as based on Hadamard matrices, a pseudo-random generator, or some other source known to those skilled in the art. In some embodiments the subset of transducer elements may be all of the transducer elements. Alternatively, in some embodiments, the subset of transducer elements may be more than one, but less than all of the transducer elements, e.g., one-half of the transducer elements.

Figure 4:
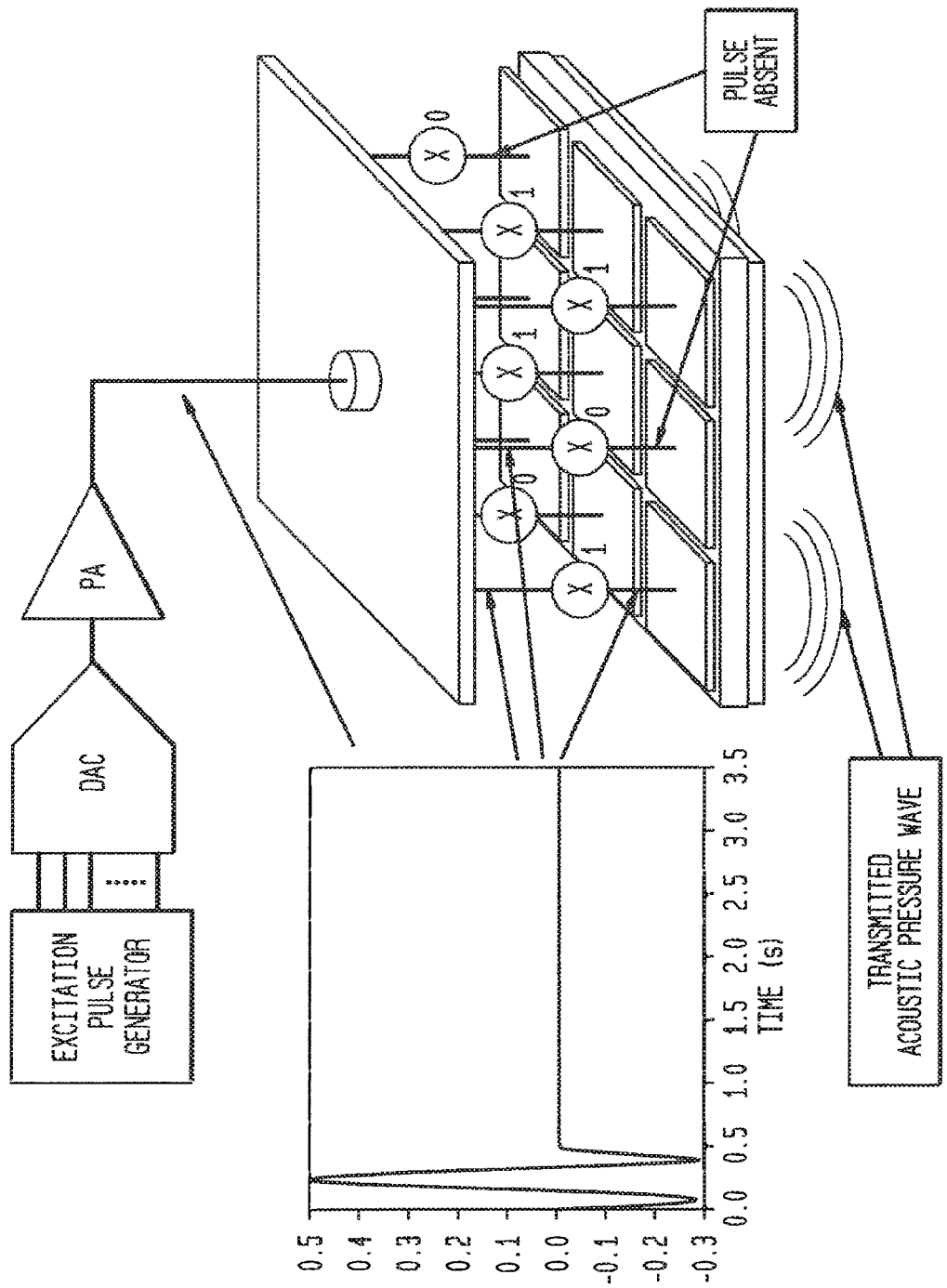
FIG. 4 shows an example of a waveform during the transmission phase.

FIG. 4 illustrates an example of the excitation pulse (Tx) as applied to a pseudo-random subset of transducer elements, according to an embodiment of the present disclosure. As shown in FIG. 4, a single excitation pulse (illustrated to the left of the transducer elements) may be generated. Each modulation unit (x) in the integrated circuit, which corresponds to a transducer element, may be configured to modulate the excitation pulse. In the embodiment of FIG. 4, the modulation units (x) may be modulating the excitation pulse with a coefficient $b_{ij}$ of 0 or 1. As such, the excitation pulse may be transmitted only to the subset of transducer elements corresponding to a modulation coefficient of 1 as illustrated.

After transmission of the excitation pulse to the subset of transducer elements, echo signals are received. During the echo receive operation (Rx), received signals from transducer elements are modulated via the corresponding modulation unit (x) with $b_{ij}=\{-1,1\}$. The modulation signals $b_{ij}(t)$ may be square waves with amplitude changing between 1 and −1 (i.e., these changing amplitudes act as the modulation coefficients). The modulation coefficients $b_{ij}$ may be chosen in a pseudo-random manner with a period less than or equal to the sampling period $T_s=1/f_s$. Alternatively, the modulation coefficients may be chosen as elements of mutually orthogonal vectors (e.g., first L vectors of N×N Hadamard matrix).

Figure 5:
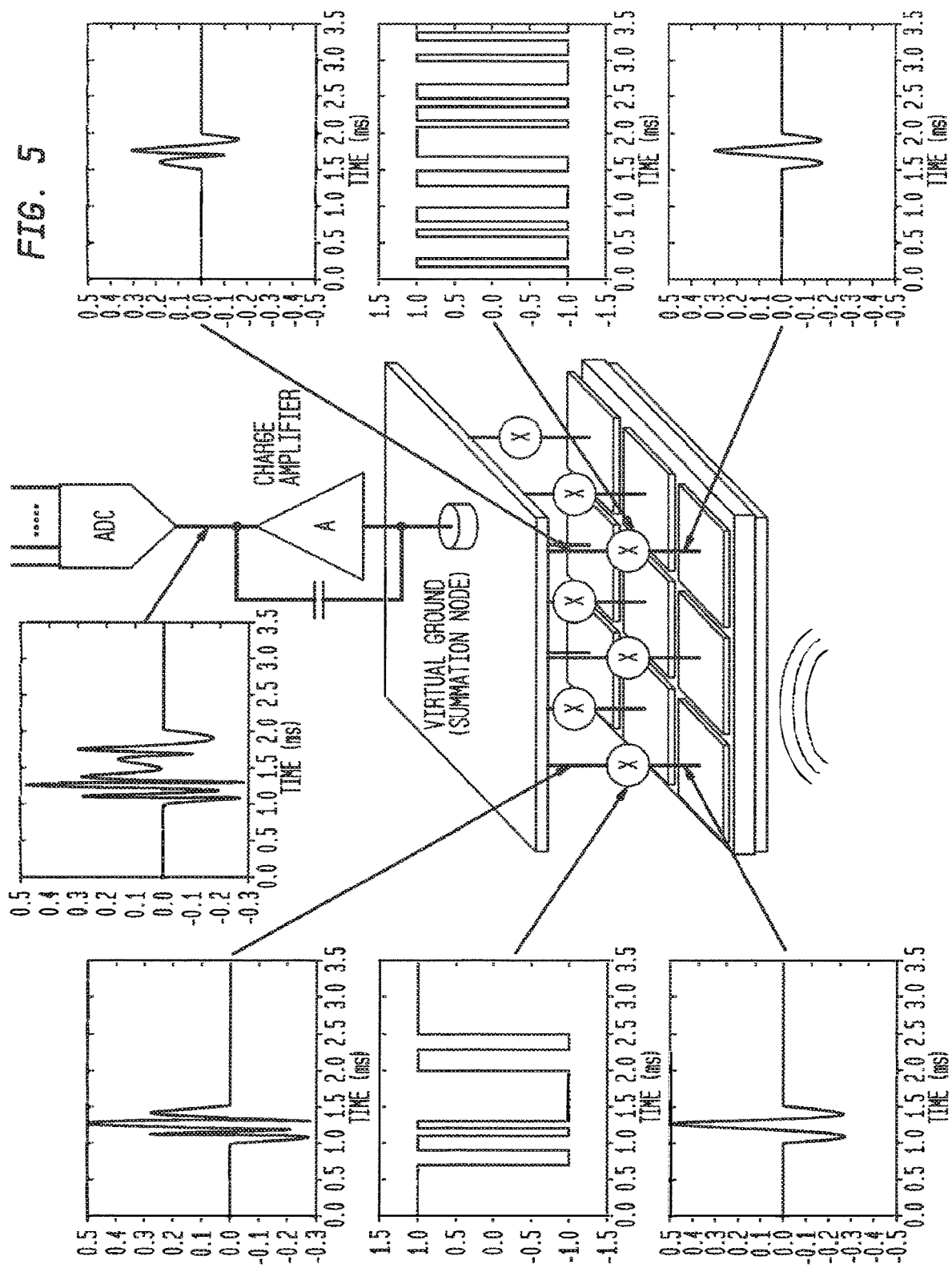
FIG. 5 shows an example of modulation of received echo signals, according to an embodiment of the present disclosure.

After the received echo signals are modulated, they may be summed up in a low-noise charge amplifier FIG. 5 illustrates an example of modulation and summation of received echo signals from the subset of transducer elements. As shown in FIG. 5, each echo signal received from a transducer element may be modulated by a corresponding square modulation wave having modulation coefficient values of 1 or −1. The modulated echo signals may be summed as they pass through a summation node and charge amplifier.

Returning to FIG. 2, the summed output from the charge amplifier may be converted to digital form using an analog-to-digital converter (ADC) and passed to an image reconstruction module operating according to a reconstruction algorithm. The image reconstruction can be implemented on either a local computational engine or on remote cloud computing servers for further power and form factor reduction.

In embodiments of the present disclosure, several methods may be implemented for reconstructing (or decoding) the computational ultrasound image from the signal channel Q(t). In some embodiments, the signal Q(t) after the sampling operation and analog-to-digital conversion can be described as a pNx1 vector signal $Q=[Q^1(0) \ldots Q^1((N-1)T_s) Q^2(0) \ldots Q^2((N-1)T_s) \ldots Q^P(0) \ldots Q^P((N-1)T_s)]^T$, where the sample $Q^1(nT_s)$ represents a signal sample at time instant nTs during the $i^{th}$ observation, p is the total number of independent observations, and N is the total number of samples during a single observation.

The received signal vector Q can be described in matrix notation as in Equation (4), identified below, where the known imaging matrix Π represents a combination of transmitted excitation waveform matrix, propagation matrix, and beamforming function, vector A is a column vector of reflectance coefficients $a_{ij}$, and W is a column vector of AWG noise samples.

$$Q_{pN\times 1} = \Pi_{pN\times M} A_{M\times 1} + W_{pN\times 1} \quad (4)$$

The imaging matrix Π of size pN by M, where M is the total number of imaged sampling grid points, contains a total of p submatrices $\Pi^i$ of size N by M each corresponding to one of the observations as shown below in Equation (5).

$$\Pi_{pN\times M} = \begin{bmatrix} \Pi^1_{N\times M} \\ \vdots \\ \Pi^p_{N\times M} \end{bmatrix} \quad (5)$$

In some embodiments of the ultrasound imaging system, the submatrices $\Pi^j$ are precalculated and stored in memory for a given excitation pulse, set of transmission and receive modulation coefficients, and sampling grid locations. Assuming a non-dispersive imaging target, the (n+l,k) element of the submatrix $\Pi^j$ can be calculated, for example, as in Equation (6), identified below, where $0 \le n \le N-1$ and $1 \le k \le M$.

The $R_s(0)$ term in Equation (6) is the energy of the transmitted excitation pulse s(t) $[H^j]$n+1,i is the modulation coefficient corresponding to the n+1$^{th}$ time sample and i$^{th}$ transducer element during the echo receive operation of the j$^{th}$ observation m$^{th}$ is the transmission modulation coefficient corresponding to the j$^{th}$ observation and m$^{th}$ transducer element s'(t) is the normalized excitation pulse transmitted by the transducers. $T_s$ is the sampling period and $t_{mki}$ is the round-trip propagation delay from the m$^{th}$ transducer to the k$^{th}$ sampling grid point and back to the i$^{th}$ transducer $r(t_{mki})$ is the propagation loss along the propagation distance equal to $V_s t_{mki}$. The constant time delay $\Delta$ and the total number of samples N are chosen such that the reflected echo signals from all of the sampling grids points are entirely received with the minimal number of samples (i.e., $\Delta \le \min(t_{mki})$ and $\ge (\max(t_{mki}) - \Delta + T_p)/T_s$, where $T_p$ is the duration of the excitation pulse s(t)).

$$[\Pi^j]_{n+1,k} = \sqrt{R_s(0)} \Sigma_{i=1}^L [H^j]_{n+1,i} \Sigma_{m=1}^L \Gamma_m^{j} s'(nT_s + \Delta - t_{mki}) r(t_{mki}) \quad (6)$$

The precalculated matrices $\Pi^j$ are then used to form the imaging matrix $\Pi$, which is then stored in a memory of the image reconstruction module for image decoding purposes. In another embodiment of the computational ultrasound imaging system, the imaging matrix H may be estimated (instead of precalculated) by imaging a known target.

Given the imaging matrix n and received signal vector Q, vector A can be estimated by using convex optimization algorithms. In one embodiment of the ultrasound imaging system, decoding is based on a linear least-squares (LS) minimum variance estimator $\hat{A}_{Mx1}$, whose estimation error is equal to the CRLB previously discussed, which is shown in Equation (7), where $\Theta$ represents a reconstruction or decoding matrix. The corresponding covariance matrix of the estimator is shown below in Equation (8).

$$\hat{A}_{Mx1} = (\Pi^T \Pi)^{-1} \Pi^T Q_{pNx1} = \Theta Q_{pNx1} \quad (7)$$

$$C_A = \frac{1}{p} I^{-1}(A) = E\left[ (\Pi^T \Pi)^{-1} \Pi^T W W^T \Pi ((\Pi^T \Pi)^{-1})^T \right] = \sigma^2 (\Pi^T \Pi)^{-1} \quad (8)$$

Since $\Pi$ and $\Theta$ are constant for a given system and imaging scenario, the image reconstruction is implemented as a single matrix multiplication between $\Theta$ and the received vector $Q_{pNx1}$.

Figure 6A:
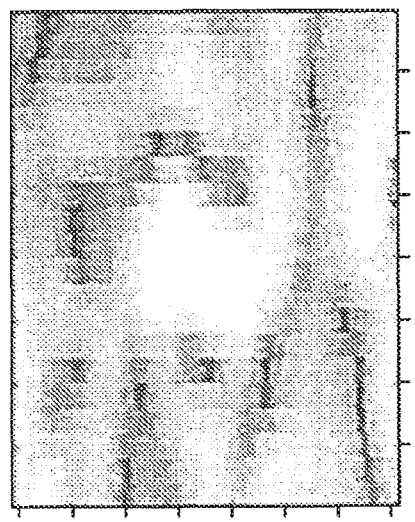
FIGS. 6A-C show a comparison of ultrasound images from embodiments disclosed in this specification and a conventional ultrasound.
Figure 6B:
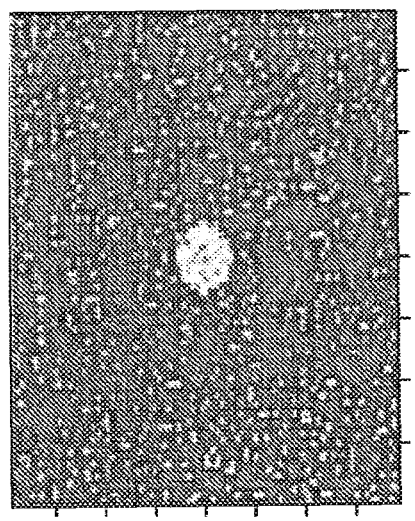
Figure 6C:
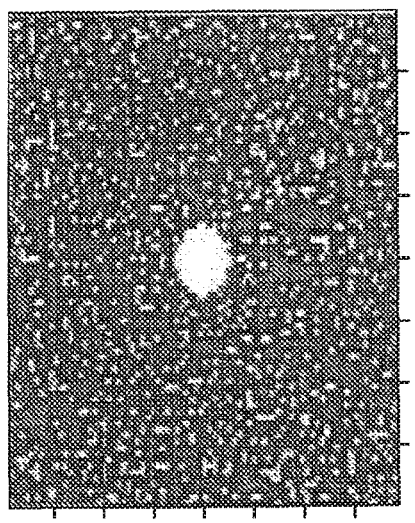

FIGS. 6A-C show preliminary simulation results using Field II acoustic package in MATLAB [28]. FIGS. 6A-C compare ultrasound images obtained from embodiments disclosed herein (FIG. 6B) at $\lambda/8$ resolution with conventional ultrasound images (FIG. 6C) of a hyperechoic cyst with a diameter of 1.5$\lambda$ in a speckle background with density of 10 scatterers per square wavelength (FIG. 6A). As shown in FIG. 6B, the ultrasound system is able to distinguish between the cyst and background scatterers, while the image obtained by the conventional ultrasound (FIG. 6C) exhibits a strong speckle noise without a clear view of the cyst region. Accordingly, FIGS. 6A-C confirm that the ultrasound system described herein is capable of achieving sub-wavelength resolution, while reducing the sidelobe artifacts and speckle noise.

Moreover, as previously discussed, further improvements in the resolution and/or image quality are expected if there is more information available about the estimated parameters such as sparsity in some domain (e.g., either spatial or frequency domain) [11]-[12]. Accordingly, in some embodiments of the ultrasound imaging system, the image decoding algorithm may be utilizing an additional sparsity-promoting L1-norm regularized cost as described in Equation (9), identified below, where a is a sparsity-controlling parameter typically chosen via cross-validation [29]-[30].

Figure 7A:
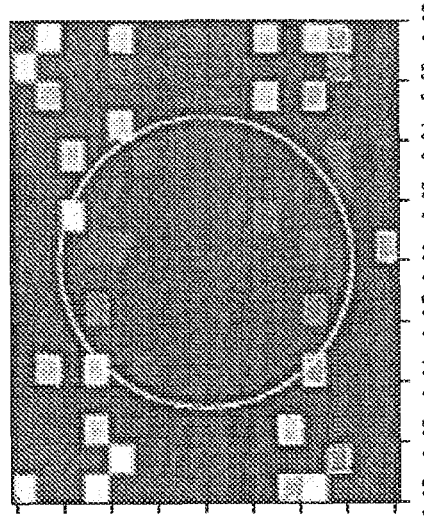
FIGS. 7A-C show a comparison of ultrasound images obtained according to examples described in this specification.
Figure 7B:
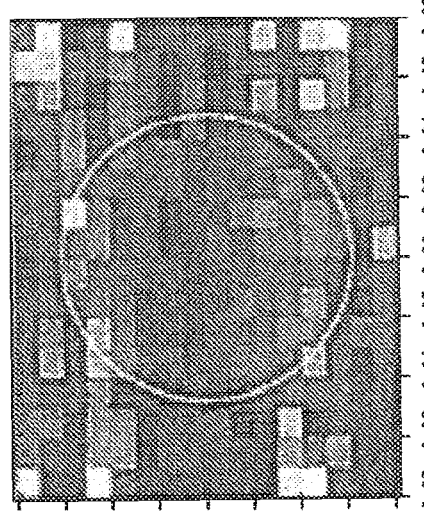
Figure 7C:
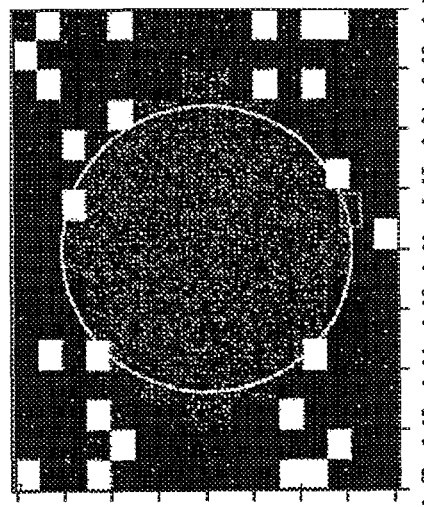

FIGS. 7 A-C illustrate a comparison between the images obtained from embodiments of the ultrasound system disclosed herein utilizing the sparsity-agnostic LS estimation method as described in Equation (7) and the method described in Equation (9). FIG. 7A shows a 1.5$\lambda$ diameter hypoechoic cyst in a speckle background. FIG. 7B shows the cyst of FIG. 7A imaged utilizing the least-square estimation method. FIG. 7C shows the cyst of FIG. 7A imaged utilizing addition $L_1$-noun cost for eSNR=6 dB, L=32, range distance of 9 cm, and $f_0$=2 MHz, and d=$\lambda$. As expected, the signal adaptive method that leverages a priori knowledge about the reflectance field, results in enhanced de-noising with a consequent reduction in estimation error and improved contrast resolution.

$$\hat{A}_{Mx1} = \underset{A_{Mx1}}{\operatorname{argmin}} \{ \| Q_{pNx1} - \Pi_{pNxM} A_{Mx1} \|_2 + \alpha \| A_{Mx1} \|_1 \}, \quad (9)$$

$$\text{s.t.} \; -1 \le A_{Mx1} \le 1$$

Even though the minimum variance image reconstruction in Eq. (7) entails a single matrix multiplication, it may still pose a challenge for real-time (e.g., 30 frames/sec) ultrasound imaging on mobile platforms. Also, if some of the acquisition-system conditions change, then so does the reconstruction matrix $\Theta$ and one needs to solve a large-scale overdetermined LS problem again. To ensure the computational load remains at an affordable level, the dimensionality of the problems defined in Equations (7) and (9) may be reduced while guaranteeing a controllable penalty in estimation error. This way, the computational load (or imaging speed) can be efficiently traded for image quality as allowed and/or required by a specific imaging application.

Going back to the potentially highly overdetermined (pN>>M) LS image reconstruction task in Equation (7), randomized numerical linear algebra may be used to discard all but the most informative subsets of measurements in $Q_{pNx1}$, based on (random) sub sampling or data sketching [31]-[32]. The target number of measurements retained is a function of the desired image quality, real-time constraints, and the available computational budget. The basic premise of the data sketching techniques is to largely reduce the number of rows of and prior to solving the LS problem in Equation (5), while offering quantifiable performance guarantees of the solution to the reduced problem [33] A data-driven methodology of keeping only the "most" informative rows relies on the so-termed (statistical) leverage scores, which are then used to define a sampling probability distribution over the rows of $\Theta$. Remarkably, results in [33] assert that performance of leverage score-based sampling degrades gracefully after reducing the number of equations. Unfortunately, their complexity is loaded by the leverage scores computation, which, similar to [34], requires SVD computations—a cumbersome (if not impossible or impractical) task for cases where M and Np are large. One can avoid computing the statistical leverage scores by pre-multiplying Θ and Π with a suitable random Hadamard transform, and then uniformly subsampling a reduced number of rows [33].

With regards to Equation (9) being convex, iterative solvers are available including interior point methods and centralized online schemes based on (sub)gradient based recursions [35]. For big data however, off-the-shelf interior point methods may be too demanding computationally, and are not amenable to decentralized or parallel implementations [33]. Subgradient-based methods are structurally simple but are often hindered by slow convergence due to restrictive step size selection rules. To address these issues, real-time algorithms as described in [36-39] could be used for L1-norm minimization described in Equation (9). These algorithms offer great promise for imaging systems, especially for situations in which measurements are stored in the cloud, or, are streamed in real time and decoding must be performed "on-the-fly" as well as without an opportunity to revisit past measurement [40].

In terms of the computation involved for image reconstruction, the ultrasound system disclosed herein allows flexible, controlled tradeoff between computation costs and some quality factor. In one embodiment, a portable system uses low-power hardware which works for a hand-held device with a lower image resolution display. In another embodiment, the computation algorithm and implementation can be dynamically adjusted to favor speed over image quality, for instance, during video mode and provide slower computation for still image of a higher resolution and image quality. This provides a smooth video mode with optional pause and zoom/enhance option.

While general-purpose computers are flexible when implementing any computation algorithms, the price for this flexibility is the (sometimes extremely) low efficiency. There are a variety of special purpose accelerators. Matrix multiplication is a common target of acceleration, though memory bandwidth tends to be an issue limiting FPGA style accelerators [41-44]. The image reconstruction of the ultrasound system lends itself to a special purpose accelerator design, where numerical calculations need not conform to industry standards usually designed to be general purpose. For example, instead of a fixed precision such as double-precision floating-points, a number of increasingly simplified options will be embodiments of this design style: (1) special floating point representation with custom mantissa and exponent, especially allowing for de-normal representation to simplified hardware, (2) reduced operand width such as half-precision floating-point, and (3) fixed-point (including integer) representation. Another embodiment of special accelerator support is dynamic reconfiguration between different embodiments as listed above. A final embodiment exploits the sparsity to reduce communication and computation demands. All these designs can improve cost, energy, and portability 'with negligible or acceptable impact on some figure of merit of the resulting image or video.

Further to the discussion with respect to FIG. 1, the following is a detailed derivation of the CRLB for the variance of the estimation error and imaging resolution of the conventional ultrasound imaging system shown in FIG. 1.

After a single plane-wave excitation s(t) transmitted by the array, the received signal at the $k^{th}$ element of the transducer array is equal to, $$q_k(t) = a_1 s(t-t_{1k}) + a_2 s(t-t_{2k}) + \ldots + a_M s(t_s-t_{Mk}) + w(t) \quad (10)$$

where w(t) is a zero-mean additive white Gaussian (AWG) noise, tjk is the propagation time from the scatterer at (zi,yi) with reflectance coefficient aj to the kth transducer element. After the sampling operation, the received signal can be represented as in Equation (11), shown below, where n–0, 1, . . . , N–1 The total number of samples N is chosen large enough so that the waveforms from all the point scatterers are entirely received.

$$q_k(nT_s) = a_1 s(nT_s - t_{1k}) + \ldots + a_M s(nT_s - t_{Mk}) + w(nT_s) = s(nT_s;a) + w(nT_s) \quad (11)$$

The vector of reflectance coefficients $a = [a_1\ a_2\ \ldots\ a_M]^T$ is a deterministic vector parameter to be estimated. From Equation (11), we see that the estimation of a belongs to a class of linear estimation problems in the presence of AWG noise. The CRLB for the estimation error of the parameters a, can be calculated as in Equation (12), shown below, where I(a) is the Fisher information matrix of the signal received by the entire array and $[.]_{ij}$ indicates $j^{th}$ diagonal element. Since the received signals at different elements of the array are independent observations of a, the Fisher information matrix of the array can be represented as the sum of Fisher information matrices of the individual transducer elements. The observations are independent and may be repeated p times, reducing the error by a factor of p.

$$\mathrm{var}(\hat{a}_j - a_j) \geq \frac{1}{p}[I^{-1}(a)]_{jj} = \frac{1}{p}\left[\left(\sum_{k=1}^{L} I_k(a)\right)^{-1}\right]_{jj} \quad (12)$$

The elements of the Fisher information matrix of the individual transducer channels can be calculated as in Equation (13), shown below, where $\sigma^2$ is the total noise paver within the sampling bandwidth $f_s = 1/T_s$.

$$[I_k(a)]_{ij} = \frac{1}{\sigma^2} \sum_{n=0}^{N-1} \frac{\partial q_k(nT_s)}{\partial a_i} \frac{\partial q_k(nT_s)}{\partial a_j} = \frac{1}{\sigma^2} \sum_{n=0}^{N-1} s(nT_s - t_i) s(nT_s - t_j) \quad (13)$$

If we assume that the sampling period is small enough, the summation term in Equation (13)can be expressed in terms of normalized autocorrelation function of the excitation waveform $R'_s(\tau)$ and echo-SNR (eSNR) defined as the ratio of the excitation waveform energy $R_s(0)$ and the noise power spectral density $N_0 = \rho^2 T_s$.

$$[I_k(a)]_{ij} = \frac{1}{\sigma^2 T_s} R_s(t_i - t_j) = \frac{R_s(0)}{\sigma^2 T_s} R'_s(t_i - t_j) = eSNR * R'_s(t_i - t_j) \quad (14)$$

If we now assume that the point-scatterers are in the far-field, the elements of the Fisher information matrix can be calculated as in Equation (15), where NA is the numerical aperture, d' is the sampling grid spacing (or resolution) normalized to the wavelength of the excitation waveform, $f_0$ is the center frequency of the excitation waveform, L is the total number of array elements, and M is the number of observed grid points along the y-axis at the radial distance $Z_i$.

$$[I_k(a)]_{ij} = eSNR * R'_s\left((j-i)\frac{NAd'}{f_0(L-1)}(2k-1+2d'(M-(i+j-1)))\right), \quad (15)$$

$$k = 1, 2, \ldots L; \quad i, j = 1, 2, \ldots M$$

A goal is to determine the relationship between the estimation error var(aj−aj) and the imaging system parameters such as NA, resolution d, eSNR, and bandwidth of the excitation waveform. Even though the Fisher information matrix 1(a) is a real-symmetric Toeplitz matrix, finding an analytical faun for the $j^{th}$ diagonal element of its inverse is a non-trivial task in general. Assuming that the excitation signal is a finite length (K-cycles) sinusoidal waveform with frequency $f_0$ and period T as in Equation (16), the normalized autocorrelation function of the excitation signal is calculated in Equation (17). Also, the fractional bandwidth $BW_\%$ of the excitation waveform is shown in Equation (18), where $BW_{RMS}$ is its root-mean-squared bandwidth, vs is the speed of sound in the imaging medium, and $\lambda = V_s/f_0$.

$$s(t) = \begin{cases} \sin(2\pi f_0 t), & -KT/2 \leq t \leq KT/2 \\ 0, & \text{otherwise} \end{cases} \quad (16)$$

$$R'_s(t) = \begin{cases} \left(1 - \frac{t}{KT}\right)\cos(2\pi f_0 t) + \frac{1}{4\pi K}\sin(2\pi f_0 t), & -KT \leq t \leq KT \\ 0, & \text{otherwise} \end{cases} \quad (17)$$

$$BW_\% = \frac{BW_{RMS}}{f_0} = \frac{BW_{RMS}\lambda}{v_s} = \frac{1}{2K} \quad (18)$$

Given the normalized autocorrelation function from Equation (17), the diagonal elements of the inverse Fisher information matrix $I^{-1}(a)$ can be numerically calculated. It can be shown that the diagonal element corresponding to the center grid point $(z_i, y_{(M+1)}/2)$ dominates other terms indicating maximum estimation error. For this reason, attention may be focused to this worst-case scenario.

Using curve fitting we show that the CRLB associated to the center grid point $(Z_i, y_{(M+1)}/2)$ can be expressed as in Equation (19), where aSNR=L*p*eSNR represents a total SNR received by the array during p observations, $D_{Abbe}$ is the Abbe diffraction limit of the imaging system defined as $\lambda/2NA$, and $S_r$ is the range resolution defined as $v_s/2BW_{RMS}$.

$$\text{var}(\widetilde{a}_j - a_j) \geq \frac{K \cdot \lambda}{L \cdot NA \cdot d \cdot eSNR} = \frac{1}{BW_\% \cdot aSNR} \frac{D_{Abbe}}{d} = \frac{S_r}{NA \cdot d \cdot aSNR} \quad (19)$$

Since the reflectance coefficients ai assume values in the range of [−1, 1], the peak imaging SNR, often referred to as Cotrast Resolution (CR), can be defined as pSNR=

$$\frac{\max(a_j)^2}{\text{var}(\widetilde{a}_j - a_j)} = 1/\text{var}(\widetilde{a}_j - a_j).$$

From the CRL of the reflectance parameters, one can readily obtain the fundamental limit on image resolution d, as shown in Equation (20).

$$d(CR) \geq \frac{CR}{aSNR}\frac{D_{Abbe}}{BW_\%} = \frac{CR}{aSNR}\frac{S_r}{NA} \quad (20)$$

In order to achieve spatial resolutions below diffraction limit with an imaging system of the type described above, the transducer array should have a dimensionality that is one less than the dimensionality of an imaged object (i.e., to image a 3D object, the transducer elements must be arranged in a 2D array). Otherwise, if a 1D transducer array is used to image 2D slices of a 3D object, the spatial resolution of the system becomes limited by the so-called elevation resolution, which is defined by the diffraction limit of an acoustic lens used for beam confinement in the elevation direction (i.e., the resolution becomes limited by the beamwidth in the elevation direction). Therefore, if an imaging system equipped with a 1D array is used to image 3D objects, no major spatial resolution improvement is expected over the traditional 2D US systems. Even though recent developments in device manufacturing promise better scalability and ability for mass production of less expensive 2D arrays, their manufacturing cost still remains high with respect to the present state of technology. Therefore, the majority of commercially available B-mode US systems are believed to be 2D systems employing 1D arrays. Nevertheless, even if the embodiments described in this disclosure use 1D transducer arrays rather than 2D arrays may not be able to achieve sub-wavelength resolution in the elevation direction, their pseudo-random beamforming function may still be utilized to significantly reduce the complexity of the traditional 2D US systems. In addition, the pseudo-random apodization (or pseudo-random selection of transducer elements) during the pulse transmission, as described above, promises a significant reduction of the sidelobe artifacts and speckle noise.

Figure 9:
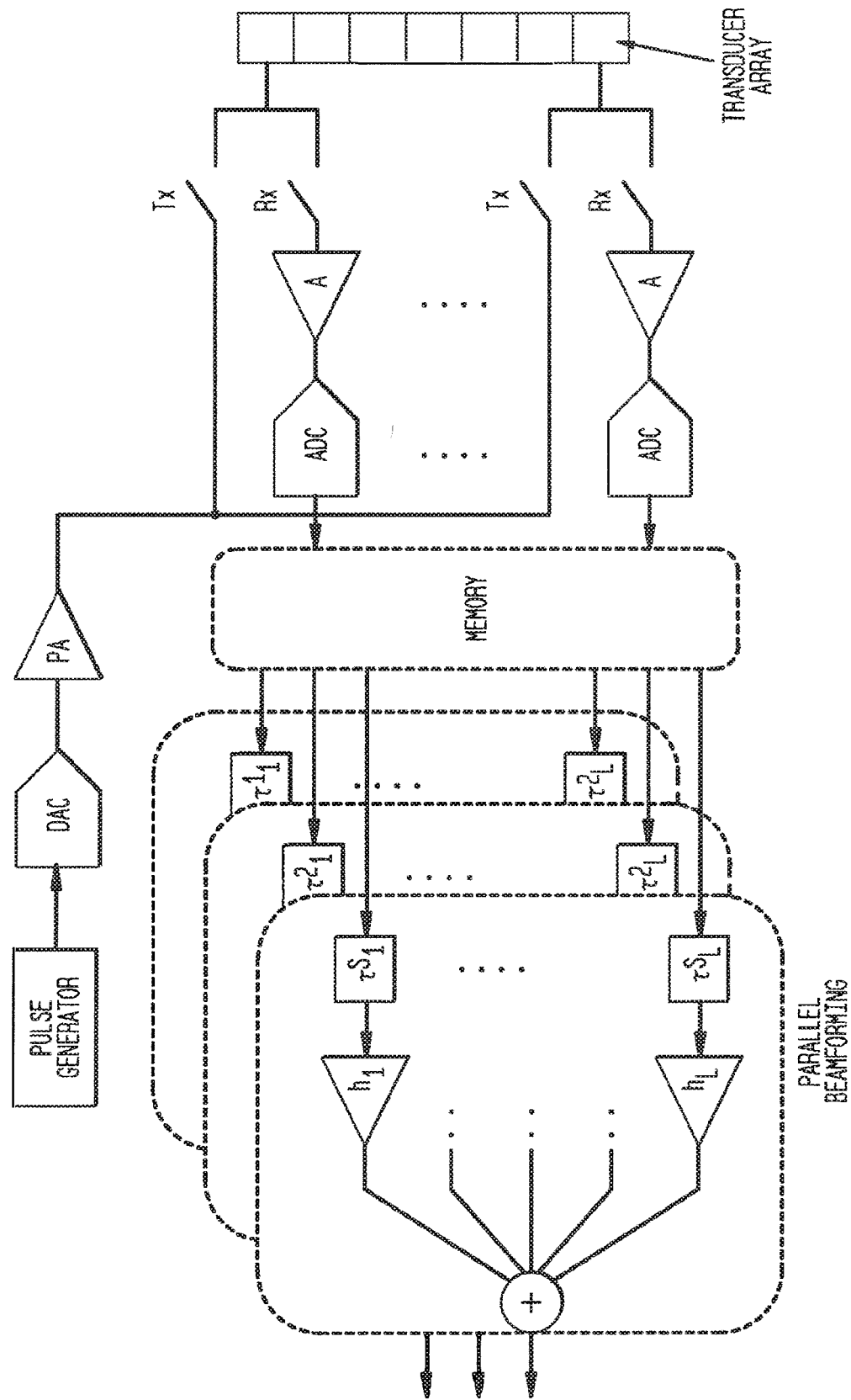
FIG. 9 shows a block diagram of a conventional B-mode ultrasound imaging system with parallel beamforming.

FIG. 9 depicts a block schematic of a typical B-mode US system utilizing parallel beamforming. Similar to the traditional B-mode US, each channel is equipped with a complex signal processing chain (e.g., low-noise amplifier A, A/D converter ADC, and a respective beam forming circuit path for each of the transducers), which does not favor portable battery-operated implementations and further scaling to larger arrays.

Parallel beamforming methods commonly use a plane-wave excitation to illuminate imaged object and then record returned echoes from all of the elements of the array (RF data). The RF data is then passed to the image reconstruction algorithm that performs beamforming (e.g., delay-and-sum) for each scan line in parallel. This operation is performed in digital domain, so that the overall imaging speed is independent of the number of scan lines and the fame rates may exceed that of traditional B-mode US systems by two orders of magnitude.

Figure 10:
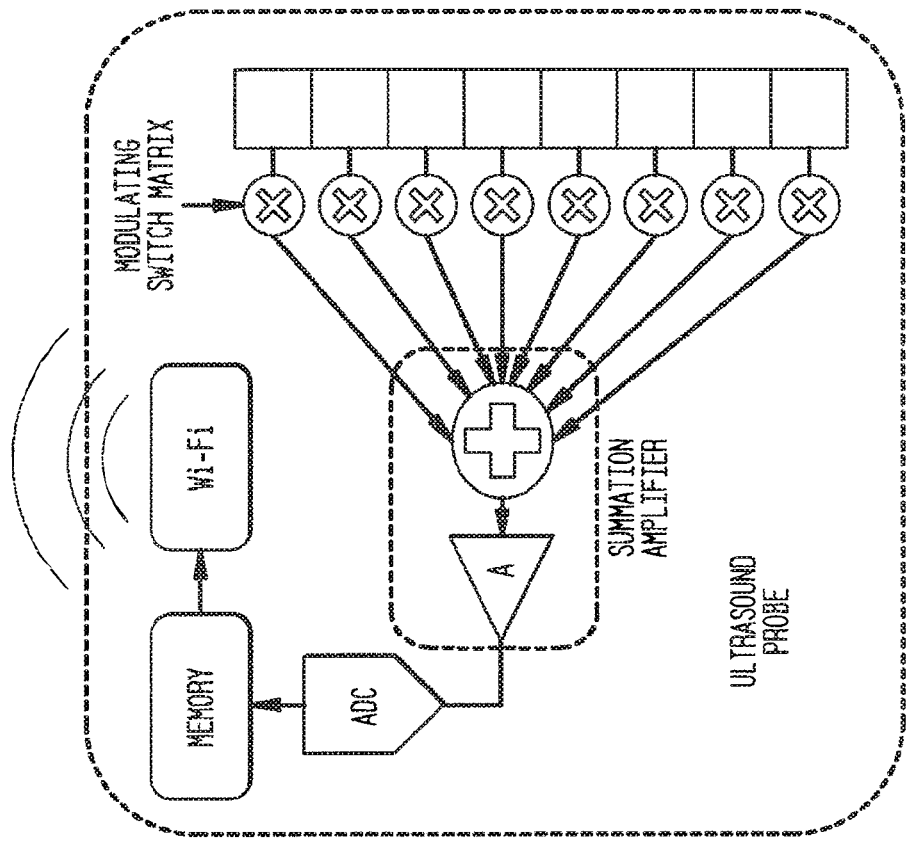
FIG. 10 shows a block diagram of an ultrasound system according to an embodiment of the present disclosure that employs a decompression algorithm to recover original transducer signals (or RF data) before they are passed to conventional beamforming algorithms such as for parallel beamforming.
Figure 10:
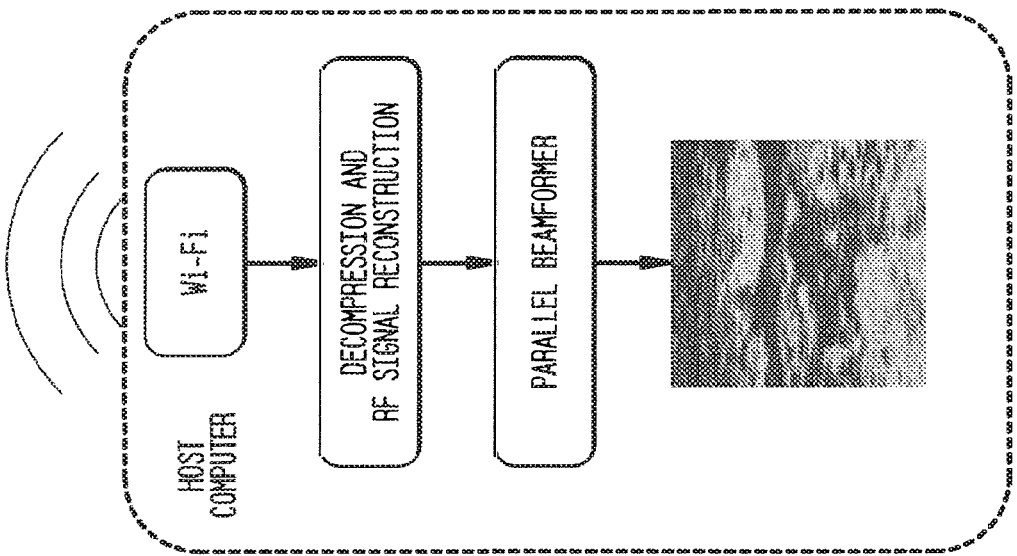

As depicted in FIG. 10, in one embodiment of the present disclosure the received echo signals from each of the transducers in the array are modulated with a pseudo-random sequence of 1's and −1's by a modulating switch matrix (X) before they are summed up into a single channel by a combiner circuit labeled summation amplifier. The resulting analog signal is then converted o digital form by an ADC circuit and stored in a memory and/or wirelessly or otherwise transmitted to a host computer for image reconstruction by a decompression and RF signal reconstruction module that feeds its output into a parallel beamformer generating images of the target. Due to a much reduced channel count achieved by the compressive nature of pseudo-random beamforming (or modulation with 1's and −1's), the total data produced by the transducer array during a single target illumination and subsequent signal acquisition is significantly reduced as compared to traditional B-mode US systems, which permits more compact designs with reduced memory size and/or network throughput requirements. In this embodiment of the present disclosure, the highly compressed single channel data after the modulation and combining operation is passed to a "decompression" algorithm that recover the RF data before it is subjected to a traditional beamforming techniques such parallel beamforming algorithm. A variety of decoding/optimization algorithms such as constrained least-squares (LS) estimation algorithm and L1-norm minimization algorithm can be used for decompression algorithm implementation. The following equation describes a constrained LS algorithm that may be used to recover highly oversampled RF data qLxN, $$\hat{q}_{LxN} = \underset{q_{LxN}}{\operatorname{argmin}} \{\|Q_{Nx1} - \operatorname{diag}(H_{NxL} q_{LxN})\|_2\}, \quad (21)$$

$$\text{s.t. } W^1_{LxL} \hat{q}_{LxN} W^2_{NxN} = \alpha \hat{q}_{LxN}$$

where $Q_{Nx1}$ is the received single channel data, $H_{nxL}$ is the LTV beamforming matrix, $W^1_{LxL}$ is the band-limitation matrix across the transducer array elements, and $W^2_{NxN}$ is the band-limitation matrix across the time samples. After the decompression step, the estimated RF data may then be passed to a conventional parallel beamforming engine to calculate reflectance coefficients (or brightness) of the imaged target.

Typical parallel beamforming systems utilize plane-wave excitation for tissue (target) illumination, where all transducer elements are simultaneously pulsed. As described literature, the plane-wave illumination associated with parallel beamforming systems may result in significantly increased side-lobe artifacts as compared to traditional B-mode US systems, which predominantly utilize focused pulse excitation. To mitigate the side-lobe artifacts, a pseudo-random pulse excitation of the type the embodiments of this disclosure employ may be used. For example, during a single target illumination, a random subset of the transducer array elements will be selected for target illumination. Each selected element would transmit the same phase excitation pulse and the target illumination will be repeated each time with a different randomly selected subset of transducer elements. Due to this additional diversity provided by this "randomized apodization" on the transmission, it is expected that the sidelobe artifacts will be reduced after repeated target illumination and subsequent averaging of individual B-mode frames. For the same reason, it is expected that the speckle noise may be significantly reduced. It should be noted that this pseudo-random apodization on pulse transmission only requires a simple switch matrix for its implementation without adding much complexity to the analog front-end.

The embodiments and examples above are illustrative, and many variations can be introduced to them without departing from the spirit of the disclosure or from the scope of the appended claims. For example, elements and/or features of different illustrative and exemplary embodiments and figures herein may be combined with each other and/or substituted with each other within the scope of this disclosure. The objects of the invention, along with various features of novelty, which characterize the invention, are pointed out with particularity in the claims annexed hereto and forming a part of this disclosure. For a better understanding of the invention, its operating advantages and the specific objects attained by its uses, reference should be made to the accompanying drawings and descriptive matter.

REFERENCES LIST A

[1] AAPMiRSNA Physics Tutorial for Residents: Topics in US B-mode US: Basic Concepts and New Technology.

[2] R. Kazys, L. Svilainis, and L. Mazeika, "Application of orthogonal ultrasonic signals and binaural processing for imaging of the environment," Ultrasonics, vol. 38, no. 1-8, pp. 171-175, March 2000.

[3] Parker, Kevin J., "Superresolution imaging of scatterers in ultrasound B-scan imaging," The Journal of the Acoustical Society of America, 131, 4680-4689 (2012).

[4] Jensen, J. A., "Deconvolution of ultrasound images," Ultrasonic Imaging, Vol. 14, Issue 1, pp. 1-15, 1992.

[5] Alam, S. K., Ophir, J., Cespedes, I., and Varghese T "A deconvolution filter for improvement of time-delay estimation in elastography," IEEE Trans. Ultrason. Ferroelectr. Freq. Control 45, pp. 1565-1572 (1998).

[6] Michailovich, O., and Adam, D., "Phase unwrapping for 2-D blind deconvolution of ultrasound images," IEEE Trans. Med. Imaging 23, pp. 7-25, 2004.

[7] Shin, H. C., Prager, R., Gomersall, H., Kingsbury, N., Treece, G., and Gee, A., "Estimation of average speed of sound using deconvolution of medical ultrasound data," Ultrasound Med. Biol. 36, pp. 623-636, 2010.

[8] Synnevag, J.-F.; Austeng, A., Holm, S., "Minimum variance adaptive beamforming applied to medical ultrasound imaging," Ultrasonics Symposium, 2005 IEEE, vol. 2, no., pp. 1199, 1202, 18-21 Sep. 2005.

[9] Asl, B. M.; Mahloojifar, A., "Minimum variance beamforming combined with adaptive coherence weighting applied to medical ultrasound imaging," Ultrasonics, Ferroelectrics, and Frequency Control, IEEE Transactions on, vol. 56, no. 9, pp. 1923-1931, September 2009.

[10] Asl, B. M.; Mahloojifar, A., "Eigenspace-based minimum variance beamforming applied to medical ultrasound imaging," Ultrasonics, Ferroelectrics, and Frequency Control, IEEE Transactions on, vol. 5 7, no. 11, pp. 2381, 2390, November 2010.

[11] T. Chernyakova and Y. C. Eldar, "Fourier Domain Beamforming: The Path to Compressed Ultrasound Imaging", IEEE Transactions on Ultrasonics, Ferroelectronics, and Frequency Control, vol. 61, issue 8, pp. 1252-1267, July 2014.

[12] N. Wagner, Y. C. Eldar and Z. Friedman, "Compressed Beamfoiming in Ultrasound Imaging", IEEE Transactions on Signal Processing, vol 60, issue 9, pp. 4643-4657, September 2012.

[13] H. Liebgott, R. Prost, and D. Friboulet, "Prebeamformed rf signal reconstruction in medical ultrasound using compressive sensing," Ultrasonics, 2012.

[14] D. Friboulet, H. Liebgott, and R. Prost, "Compressive sensing for raw rf signals reconstruction in ultrasound," IEEE International Ultrasonics Symposium, 2010.

[15] C. Quinsac, A. Basarab, J. M. Girault, and D. Kouam, "Compressed sensing of ultrasound images: sampling of spatial and frequency domains," IEEE Workshop on Signal Processing Systems, 2010.

[16] C. Quinsac, N. Dobigeon, D. Kouam, and J. Tourneret, "3D compressed sensing ultrasound imaging," IEEE International Ultrasonics Symposium, 2010.

[17] R. Tur, Y. C. Eldar, and Z. Friedman, "Innovation rate sampling of pulse streams with application to ultrasound imaging," IEEE transactions on Signal Processing, 2011

[18] S. Campbell, "A Short History of Sonography in Obstetrics and Gynecology," Facts Views Vis Obgyn 2013, v 5(3): pp. 213-229.

[19] F. J. Fry, J. E. Barger, "Acoustical properties of the human skull," J. Acoust. Soc. Am. 63, 1576 (1978).

[20] P. J. White, G. T. Clement, K. Hynynen, Longitudinal and shear mode ultrasound propagation in human skull bone, Ultrasound in Medicine & Biology, Volume 32, Issue 7, July 2006, Pages 1085-1096,

[21] N. Petridou, M. Italiaander, B. L. van de Bank, J. C. W. Siero, P. R. Luijten and D. W. J. Klomp, "Pushing the limits of high-resolution functional MRI using a simple high-density multi-element coil design," NMR IN BIO-MEDICINE, ISSN 0952-3480, 01/2013, Volume 26, Issue 1, pp. 65-73.

[22] Schmutzhard, S.; Jung, A.; Hlawatsch, F., "Minimum variance estimation for the sparse signal in noise model," Information Theory Proceedings (ISIT), 2011 IEEE International Symposium on, vol., no., pp. 124, 128, Jul. 31 2011-Aug. 5 2011.

[23] Juhwan Yoo; Becker, S.; Monge, m.; Loh M., Emmami-Neyestanak, A., "Design and implementation of a fully integrated compressed-sensing signal acquisition system," Acoustics, Speech and Signla Processing (ICASSP), 2012 IEEE International conference on, vol. no., pp. 5325, 5328, 25-30 Mar. 2012.

[24] J. W. Goodman, Statistical Optics., Wiley-Interscience, New York, 1985.

[25] Burchkhardt, C. B., "Speckle in ultrasound B-mode scans," Sonics and Ultrasonics, IEEE Transactions on, vol. 25, no. 1, pp. 1, 6, January 1978.

[26] Ouyang, G. "Laser speckle reduction based on angular diversity induced by Piezoelectric Benders," JOURNAL OF THE EUROPEAN OPTICAL SOCIETY-RAPID PUBLICATIONS, ISSN 1990-2573, 2013, Vol. 8, p. 4.

[27] M. N. Akram, Z. Tong, G. Ouyang, X. Chen, and V. Kartashov, "Laser speckle reduction due to spatial and angular diversity introduced by fast scanning micromirror," Appl. Optics 49(17), 3297-3304 (2010).

[28] J. A. Jensen, "FIELD: a program for simulating ultrasound systems," in 10th Nordicbaltic Conference on Biomedical Imaging, Supplement 1, Part 1, vol. 34, 1996, pp. 351-353.

[29] T. Hastie, R. Tibshirani, and J. Friedman, The Elements of Statistical Learning, 2nd ed. New York: Springer, 2009.

[30] R. Tibshirani, "Regression shrinkage and selection via the lasso," J. Roy. Stat. Soc. B, vol. 58, pp. 267-288, 1996.

[31] M. W. Mahoney, "Randomized algorithms for matrices and data," Foundations and Trends in Machine Learn., vol. 3, no. 2, pp. 123-224, 2011.

[32] K. L Clarkson and D. P Woodmff, "Low rank approximation and regression in input sparsity time," in Proc. Symp. Theory Computing, Jun. 1-4, 2013, pp. 81-90.

[33] K. Slavakis, G. B. Giannakis, and G. Mateos, "Modeling and optimization for Big Data analytics," IEEE Signal Processing Magazine, vol 31, no. 5, pp. 18-31, September 2014.

[34] V. M. Patel, H. V. Nguyen, and R. Vidal, "Latent space sparse subspace clustering," in Proc. of Intl. Conf Computer Vision, Sydney: Australia, 2013.

[35] S. Shalev-Shwartz, "Online learning and online convex optimization," Foundations and Trends in Machine Learning, vol 4, no. 2, pp. 107-194, 2012.

[36] M. Mardani, G. Mateos, and G. B. Giannakis, "Dynamic anomalography: Tracking network anomalies via sparsity and low rank," IEEE Journal of Sel. Topics in Signal Processing, vol. 8, February 2013.

[37] M. Mardani, G. Mateos, and G. B. Giannakis, "Decentralized sparsity-regularized rank minimization: Algorithms and applications," IEEE Trans. on Signal Processing, vol. 61, pp. 5374-5388, November 2013.

[38] G. Mateos, I. A. Bazerque, and G. B. Giannakis, "Distributed sparse linear regression," IEEE Trans. Signal Processing, vol. 58, no. 10, pp. 5262-5276, October 2010.

[39] G. Mateos, I. D. Schizas, and G. B. Giannakis, "Distributed recursive least-squares for consensus-based in-network adaptive estimation," IEEE Transactions on Signal Processing, vol. 57, no. 11, November 2009.

[40] K. Slavakis, S.-J. Kim, G. Mateos, and G. B. Giannakis, "Stochastic approximation vis-a-vis online learning for Big Data," IEEE Signal Processing Magazine, vol. 31, no. 6, pp. 124-129, November 2014.

[41] F. Bensaali, A. Amira, R. Sotudeh, "Floating-point matrix product on FPGA", Proc. IEEE/ACS Int. Conf. on Computer Systems and Applications, pp. 466-473, 2007.

[42] C. Y. Lin, H. K.-H. So, P. H. Leong, "A model for matrix multiplication performance on FPGAs", Proc. International Conference on Field Programmable Logic and Applications, pp. 305-310, September 2011.

[43] J. Fowers, K. Ovtcharov, "A High Memory Bandwidth FPGA Accelerator for Sparse Matrix-Vector Multiplication", Proc. IEEE 22nd International Symposium on Field-Programmable Custom Computing Machines. pp 36-43, May 2014.

[44] Z. Jovanovic, V. Milutinovic, "FPGA accelerator for floating-point matrix multiplication", IET Computers & Digital Techniques, 6(4): 249-256.

REFERENCE LIST B

[1] AAPM/RSNA Physics Tutorial for Residents: Topics in US B-mode US: Basic Concepts and New Technology.

[2] R Kazys, L. Svilainis, and L Mazeika, "Application of orthogonal ultrasonic signals and binaural processing for imaging of the environment," Ultrasonics, vol. 38, no. 1-8, pp. 171-175, March 2000.

[3] Parker, Kevin J., "Superresolution imaging of scatterers in ultrasound B-scan imaging," The Journal of the Acoustical Society of America, 131, 4680-4689 (2012).

[4] Jensen, J. A., "Deconvolution of ultrasound images," Ultrasonic Imaging, Vol. 14, Issue 1, pp. 1-15, 1992.

[5] Alam, S. K., Ophir, J., Cespedes, I., and Varghese T. "A deconvolution filter for improvement of time-delay estimation in elastography," IEEE Trans. Ultrason. Ferroelectr. Freq. Control 45, pp. 1565-1572(1998).

[6] Michailovich, O., and Adam, D., "Phase unwrapping for 2-D blind deconvolution of ultrasound images," IEEE Trans. Med. Imaging 23, pp. 7-25, 2004.

[7] Shin, H. C., Prager, R., Gomersall, H., Kingsbury, N., Treece, G., and Gee, A., "Estimation of average speed of sound using deconvolution of medical ultrasound data," Ultrasound Med. Biol. 36, pp. 623-636, 2010.

[8] Synnevag, J.-F.; Austeng, A; Holm, S., "Minimum vanance adaptive beamforming applied to medical ultrasound imaging," Ultrasonics Symposium, 2005 IEEE, vol 2, no, pp. 1199, 1202, 18-21 Sep. 2005.

[9] Asl, B. M.; Mahloojifar, A., "Minimum variance beamforming combined with adaptive coherence weighting applied to medical ultrasound imaging," Ultrasonics, Ferroelectrics, and Frequency Control, IEEE Transactions on, vol. 56, no. 9, pp. 1923-1931, September 2009.

[10] Asl, B. M.; Mahloojifar, A, "Eigenspace-based minimum variance beamforming applied to medical ultrasound imaging," Ultrasonics, Ferroelectrics, and Frequency Control, IEEE Transactions on, vol. 57, no. 11, pp. 2381, 2390, November 2010.

[11] T. Chernyakova and Y. C. Eldar, "Fourier Domain Beamforming: The Path to Compressed Ultrasound Imaging", IEEE Transactions on Ultrasonics, Ferroelectronics, and Frequency Control, vol 61, issue 8, pp. 1252-1267, July 2014.

[12] N. Wagner, Y. C. Eldar and Z. Friedman, "Compressed Beamforming in Ultrasound Imaging", IEEE Transactions on Signal Processing, vol. 60, issue 9, pp. 4643-4657, September 2012.

[13] H. Liebgott, R. Prost, and D. Friboulet, "Prebeamformed rf signal reconstruction in medical ultrasound using compressive sensing," Ultrasonics, 2012.

[14] D. Fribouiet, H. Liebgott, and R. Prost, "Compressive sensing for raw rf signals reconstruction in ultrasound," IEEE International Ultrasonics Symposium, 2010.

[15] C. Quinsac, A. Basarab, J. M. Girault, and D. Kouam, "Compressed sensing of ultrasound images: sampling of spatial and frequency domains," IEEE Workshop on Signal Processing Systems, 2010.

[16] C. Quinsac, N Dobigeon, D. Kouam, and J. Tourneret, "3D compressed sensing ultrasound imaging," IEEE International Ultrasonics Symposium, 2010.

[17] R. Tur, Y. C. Eldar, and Z. Friedman, "Innovation rate sampling of pulse streams with application to ultrasound imaging," IEEE transactions on Signal Processing, 2011.

[18] S. Campbell, "A Short History of Sonography in Obstetrics and Gynecology," Facts Views Vis Obgyn 2013, v. 5(3): pp. 213-229.

[19] F. J. Fry, 1 E. Barger, "Acoustical properties of the human skull," J. Acoust Soc. Am. 63, 1576 (1978).

[20] P. J. White, G. T. Clement, K. Hynynen, Longitudinal and shear mode ultrasound propagation in human skull bone, Ultrasound in Medicine & Biology, Volume 32, Issue 7, July 2006, Pages 1085-1096,

[21] N. Petridou, M. Italiaander, B. L. van de Bank, J. C. W. Siero, P. R. Luijten and D. W. J. Klomp, "Pushing the limits of high-resolution functional MRI using a simple high-density multi-element coil design," NMR IN BIOMEDICINE, ISSN 0952-3480, 01/2013, Volume 26, Issue 1, pp. 65-73.

[22] Schmutzhard, S.; Jung, A.; Hlawatsch, F., "Minimum variance estimation for the sparse signal in noise model," Information Theory Proceedings (ISIT), 2011 IEEE International Symposium on, vol., no., pp. 124, 128, Jul. 31 2011-Aug. 5 2011.

[23] Juhwan Yoo; Becker, S.; Monge, M.; Loh, M.; Candes, E.; Emami-Neyestanak, A., "Design and implementation of a fully integrated compressed-sensing signal acquisition system," Acoustics, Speech and Signal Processing (ICASSP), 2012 IEEE International Conference on, vol, no., pp. 5325, 5328, 25-30 Mar. 2012.

[24] J. W. Goodman, Statistical Optics., Wiley-Interscience, New York, 1985.

[25] Burckhardt, C. B., "Speckle in ultrasound B-mode scans," Sonics and Ultrasonics, IEEE Transactions on, vol. 25, no. 1, pp. 1, 6, January 1978.

[26] Ouyang, G. "Laser speckle reduction based on angular diversity induced by Piezoelectric Benders," JOURNAL OF THE EUROPEAN OPTICAL SOCIETY-RAPID PUBLICATIONS, ISSN 1990-2573, 2013, Vol. 8, p. 4.

[27] M. N Akram, Z. Tong, G. Ouyang, X. Chen, and V Kartashov, "Laser speckle reduction due to spatial and angular diversity introduced by fast scanning micromirror," Appl. Optics 49(17), 3297-3304 (2010).

[28] J. A. Jensen, "FIELD: a program for simulating ultrasound systems," in 10th Nordicbaltic Conference on Biomedical Imaging, Supplement 1, Part 1, vol. 34, 1996, pp. 351-353

[29] J. Candes and M. B. Wakin, "An introduction to compressive sampling," IEEE Signal Processing Magazine, vol. 25, no. 2, pp. 21-30, 2008.

[30] E. J. Candes, "Mathematics of sparsity (and a few other things)," Proc. of the International Congress of Mathematicians, Seoul, South Korea, 2014.

[31] K. Slavakis, G. B. Giannakis, and G. Mateos, "Modeling and optimization for Big Data analytics," IEEE Signal Processing Magazine, vol. 31, no. 5, pp. 18-31, September 2014.

[32] T. Hastie, R. Tibshirani, and J. Friedman, The Elements of Statistical Learning, 2nd ed. New York: Springer, 2009.

[33] R. Tibshirani, "Regression shrinkage and selection via the iasso," J. Roy. Stat. Soc. B, vol. 58, pp. 267-288, 1996.

[34] B. K. Natarajan, "Sparse approximate solutions to linear systems," SIAM J. Comput., vol. 24, pp. 227-234, 1995.

[35] E. J. Candes and T. Tao, "Decoding by linear programming," IEEE Trans. Info. Theory, vol 51, no. 12, pp. 4203-4215, December 2005.

[36] E. J. Candes, J. K. Romberg, and T. Tao, "Stable signal recovery form incomplete and inaccurate measurements," Communications on Pure and Applied Mathematics, vol 59, pp. 1207-1223, 2006.

[37] N. Parikh and S. Boyd, "Proximal algorithms", Foundations and Trends in Optimization, vol. 1, no. 3, pp. 123-231, 2014.

[38] S. G. Mallat and Z. Zhang, "Matching pursuits with time-frequency dictionaries," IEEE Transactions on Signal Processing, pp. 3397-3415, December 1993.

[39] D. P. Bertsekas and J. N. Tsitsiklis, Parallel and Distributed Computation: Numerical Methods, 2nd ed. Belmont, MA: Athena-Scientific, 1999.

[40] H. Zhu, G. Leus, and G. B. Giannakis, "Sparsity-cognizant total least-squares for perturbed compressive sampling," IEEE Transactions on Signal Processing, vol. 59, no. 5, pp. 2002-2016, May 2011.

[41] M. W. Mahoney, "Randomized algorithms for matrices and data," Foundations and Trends in Machine Learn., vol. 3, no. 2, pp. 123-224, 2011.

[42] K. L. Clarkson and D. P. Woodruff, "Low rank approximation and regression in input sparsity time," in Proc. Symp. Theory Computing, Jun. 1-4, 2013, pp. 81-90.

[43] S. Shalev-Shwartz, "Online learning and online convex optimization," Foundations and Trends in Machine Learning, vol. 4, no. 2, pp. 107-194, 2012.

[44] M. Mardani, G. Mateos, and G. B. Giannakis, "Dynamic anomalography: Tracking network anomalies via sparsity and low rank," IEEE Journal of Sel. Topics in Signal Processing, vol. 8, February 2013.

[45] M. Mardani, G. Mateos, and G. B. Giannakis, "Decentralized sparsity-regularized rank minimization: Algorithms and applications," IEEE Trans. on Signal Processing, vol. 61, pp. 5374-5388, November 2013.

[46] G. Mateos, J. A. Bazerque, and G. B. Giannakis, "Distributed sparse linear regression," IEEE Trans. Signal Processing, vol. 58, no. 10, pp. 5262-5276, October 2010.

[47] G. Mateos, I. D. Schizas, and G. B. Giannakis, "Distributed recursive least-squares for consensus-based in-network adaptive estimation," IEEE Transactions on Signal Processing, vol. 57, no. 11, November 2009.

[48] K. Slavakis, S.-J. Kim, Cr. Mateos, and G. B. Giannakis, "Stochastic approximation vis-a-vis online learning for Big Data," IEEE Signal Processing Magazine, vol. 31, no. 6, pp. 124-129, November 2014.

[49] V. M. Patel, H. V. Nguyen, and R. Vidal, "Latent space sparse subspace clustering," in Proc. of Intl. Conf. Computer Vision, Sydney: Australia, 2013.

[50] F. Bensaali, A. Amira, R. Sotudeh, "Floating-point matrix product on FPGA", Proc. IEEE/ACS Int. Conf. on Computer Systems and Applications, pp. 466-473, 2007

[51] C. Y. Lin, H. K.-H. So, P. H. Leong, "A model for matrix multiplication performance on FPG-As", Proc. International Conference on Field Programmable Logic and Applications, pp. 305-310, September 2011.

[52] J. Fowers, K. Ovtcharov, "A High Memory Bandwidth FPGA Accelerator for Sparse Matrix-Vector Multiplication", Proc. IEEE 22nd International Symposium on Field-Programmable Custom Computing Machines. pp 36-43, May 2014

[53] Z. Jovanovic, V. Milutinovic, "FPGA accelerator for floating-point matrix multiplication", IET Computers & Digital Techniques, 6(4): 249-256.

[54] Z. Ignjatovic, M. Sterling. "Information-Theoretic Approach to AID Conversion," IEEE Transactions on Circuits and Systems I: Regular Papers, v. 60, 2013, p. 2249.

[55] Marijan, M, Ignjatovic, Z, "Non-Linear Reconstruction of Delta-Sigma Modulated Signals: Randomized Surrogate Constraint Decoding Algorithm," Signal Processing, IEEE Transactions on, vol. 61, no. 21, pp. 5361, 5373, Nov. 1, 2013.

[56] Song, Y; Gao, Z; lgnjatovic, Z. "A Low Power Linearity-Ratio-Independent DAC with Application in Multi-Bit Delta Sigma ADCs," in 53rd Midwest Symposium on Circuits and Systems (wfWSCAS 2010)., 2010, p. 481-484.

[57] M. Marijan, Z. Ignjatovic. "Code Division Parallel Delta-Sigma AID Converter with Probabilistic Iterative Decoding", IEEE International Symposium on Circuits and Systems, ISCAS 2010.

[58] Malisa Marijan, Zeljko Ignjatovic. "Reconstruction of Oversampled Signals from the Solution Space of Delta-Sigma Modulated Sequences", IEEE Midwest Symposium on Circuits and Systems 2011

What is claimed is:

1. An ultrasound imaging system comprising:
a multi-element set of ultrasound transducer elements;
an excitation pulse generator providing a succession of excitation pulses to the ultrasound transducer elements;
a receiving switch matrix modulating echoes received by the ultrasound transducer elements in response to the excitation pulses applied to an object, with a random sequence of modulation coefficients;
a circuit summing the modulated echoes in an analog domain;
and the image reconstruction processor configured to apply an imaging matrix to the summed modulated echoes to thereby generate one or more images of the object;
wherein the imaging matrix is a combination of transmitted excitation waveform matrix, propagation matrix, and beamforming function.

2. The ultrasound imaging system of claim 1, in which the receiving switch matrix modulates the echoes with modulating waveforms having irregular periods.

3. The ultrasound imaging system of claim 2, in which the modulating waveforms comprise waveforms of a succession of positive and negative levels.

4. The ultrasound imaging system of claim 3, including a differential charge amplifier, wherein the echoes modulated with the positive levels are supplied to a positive input and the echoes modulated with the negative levels are supplied to a negative input of the differential charge amplifier.

5. The ultrasound imaging system of claim 1, in which the imaging matrix is selected to relate summed echoes from a known object to an expected image of the object generated with the image reconstruction processor.

6. The ultrasound imaging system of claim 1, including an analog-to-digital converter (ADC) converting the summed modulated echoes into a digital sequence supplied to the image reconstruction processor.

7. The ultrasound imaging system of claim 1, further including a transmission switch matrix transmitting each excitation pulse only to a respective, randomly selected subset of the elements in the multi-element set.

* * * * *